United States Patent
Mistretta et al.

(10) Patent No.: US 10,368,818 B2
(45) Date of Patent: Aug. 6, 2019

(54) SYSTEM AND METHOD OF QUANTITATIVE ANGIOGRAPY

(71) Applicant: Wisconsin Alumni Research Foundation, Madison, WI (US)

(72) Inventors: Charles Mistretta, Madison, WI (US); Charles Strother, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 39 days.

(21) Appl. No.: 15/723,125

(22) Filed: Oct. 2, 2017

(65) Prior Publication Data

US 2019/0099146 A1    Apr. 4, 2019

(51) Int. Cl.
*A61B 6/00* (2006.01)
*A61B 6/03* (2006.01)
(Continued)

(52) U.S. Cl.
CPC .............. *A61B 6/507* (2013.01); *A61B 6/032* (2013.01); *A61B 6/463* (2013.01); *A61B 6/466* (2013.01); *A61B 6/504* (2013.01); *A61B 6/5217* (2013.01); *G06T 7/0016* (2013.01); *G06T 7/11* (2017.01); *G06T 11/005* (2013.01);
(Continued)

(58) Field of Classification Search
CPC ......... A61B 6/507; A61B 6/032; A61B 6/463; A61B 6/466; A61B 6/504; A61B 6/5217; G06T 7/11; G06T 7/0016; G06T 11/005; G06T 11/006; G06T 11/60;
(Continued)

(56) References Cited

U.S. PATENT DOCUMENTS 7,545,901 B2 * 6/2009 Mistretta ............... G06T 11/006
378/4
8,643,642 B2 * 2/2014 Mistretta .............. A61B 6/4441
345/419
(Continued)

OTHER PUBLICATIONS

Beijer, et al., 4D-CT Angiography Differentiating Arteriovenous Fistula Subtypes, Clinical Neurology and Neurosurgery, 2013, 115:1313-1316.

(Continued)

*Primary Examiner* — Brenda C Bernardi
(74) *Attorney, Agent, or Firm* — Quarles & Brady LLP

(57) ABSTRACT

Methods and systems are provided for generating quantitative computed tomography (CT) angiographic images using imaging systems that acquire a set of projection views forming CT angiographic image data of a patient using a projection duration of less than 50 milliseconds. The method may include producing a composite image from the CT angiographic image data that indicates an attenuation value at each composite image pixel of the patient, backprojecting each projection view in the CT angiographic image data and weighting a value backprojected into at image pixel by an attenuation value of a corresponding pixel in the composite image and summing backprojected values for each image pixel to produce a CT image of the patient. The method may further include performing a scatter correction and determining at least one of a flow direction or a velocity of flow with a vessel in the patient to provide the quantitative CT angiographic images.

33 Claims, 20 Drawing Sheets

(51) Int. Cl.
  *G06T 7/00*  (2017.01)
  *G06T 7/11*  (2017.01)
  *G06T 11/00*  (2006.01)
  *G06T 11/60*  (2006.01)

(52) U.S. Cl.
  CPC ............ *G06T 11/006* (2013.01); *G06T 11/60* (2013.01); *G06T 2207/10076* (2013.01); *G06T 2207/10081* (2013.01); *G06T 2207/30104* (2013.01); *G06T 2211/404* (2013.01)

(58) Field of Classification Search
  CPC . G06T 2207/10076; G06T 2207/10081; G06T 2207/30104; G06T 2211/404
  See application file for complete search history.

(56) References Cited

U.S. PATENT DOCUMENTS

| | | | | |
|---|---|---|---|---|
| 8,963,919 | B2* | 2/2015 | Mistretta | A61B 6/032 345/424 |
| 2003/0013953 | A1* | 1/2003 | Mistretta | A61B 6/032 600/425 |
| 2006/0120507 | A1* | 6/2006 | Brunner | A61B 6/466 378/62 |
| 2008/0118032 | A1* | 5/2008 | Graham | G21K 1/04 378/152 |
| 2011/0037761 | A1* | 2/2011 | Mistretta | A61B 6/4441 345/419 |
| 2011/0249880 | A1* | 10/2011 | Parikh | A61B 5/06 382/131 |
| 2013/0172734 | A1* | 7/2013 | Hsieh | A61B 6/032 600/425 |
| 2016/0267704 | A1 | 9/2016 | Mistretta et al. | |
| 2017/0071561 | A1* | 3/2017 | Bernhardt | A61N 5/1049 |
| 2017/0076467 | A1* | 3/2017 | Mistretta | G06T 7/246 |

OTHER PUBLICATIONS

Naimuddin, et al., Scatter-glare Correction Using a Convolution Algorithm with Variable Weighting, Medical Physics, 1987, 14(3):330-334.

* cited by examiner

SYSTEM AND METHOD OF QUANTITATIVE ANGIOGRAPY

BACKGROUND

The present invention is related to angiography and, in particular, the invention relates to a system and method for producing angiographic images using x-ray projection data, such as may be acquired using a computed tomography (CT) system.

In a computed tomography system, an x-ray source projects a fan-shaped beam which is collimated to lie within an X-Y plane of a Cartesian coordinate system, termed the "image plane." The x-ray beam passes through the object being imaged, such as a medical patient, and impinges upon an array of radiation detectors. The intensity of the transmitted radiation is dependent upon the attenuation of the x-ray beam by the object and each detector produces a separate electrical signal that is a measurement of the beam attenuation. The attenuation measurements from all the detectors are acquired separately to produce what is called the "transmission profile," or "attenuation profile" or "projection."

The source and detector array in a conventional CT system are rotated on a gantry within the imaging plane and around the object so that the angle at which the x-ray beam intersects the object constantly changes. The transmission profile from the detector array at a given angle is referred to as a "view" and a "scan" of the object comprises a set of views made at different angular orientations during one revolution of the x-ray source and detector. In a 2D scan, data is processed to construct an image that corresponds to a two dimensional slice taken through the object. The prevailing method for reconstructing an image from 2D data is referred to in the art as the filtered backprojection technique. This image reconstruction process converts the attenuation measurements acquired during a scan into integers called "CT numbers" or "Hounsfield units", which are used to control the brightness of a corresponding pixel on a display.

The filtered backprojection image reconstruction method is the most common technique used to reconstruct CT images from acquired transmission profiles. As shown in FIG. 1A each acquired x-ray transmission profile 100 is backprojected onto the field of view (FOV) 102 by projecting each ray sum 104 in the profile 100 through the FOV 102 along the same ray path that produced the ray sum 104 as indicated by arrows 106. In projecting each ray sum 104 in the FOV 102 we have no a priori knowledge of the subject and the assumption is made that the x-ray attenuation in the FOV 102 is homogeneous and that the ray sum should be distributed equally in each pixel through which the ray path passes. For example, a ray path 108 is illustrated in FIG. 1A for a single ray sum 104 in one transmission profile 100 and it passes through N pixels in the FOV 102. The attenuation value (P) of this ray sum 104 is divided up equally between these N pixels:

$$\mu_n = (P \times 1)/N \quad (1);$$

where: $\mu_n$ is the attenuation value distributed to the $n^{th}$ pixel in a ray path having N pixels.

Clearly, the assumption that attenuation in the FOV 102 is homogeneous is not correct. However, as is well known in the art, if certain corrections are made to each transmission profile 100 and a sufficient number of profiles are acquired at a corresponding number of projection angles, the errors caused by this faulty assumption are minimized and image artifacts are suppressed. In a typical filtered backprojection method of image reconstruction, anywhere from 400 to 1000 views are typically required to adequately suppress image artifacts in a 2D CT image.

There are a number of clinical applications where the time required to acquire a large number of views is not available. In time-resolved angiography, for example, a series of images are acquired as contrast agent flows into the region of interest. Each image is acquired as rapidly as possible to obtain a series of snapshots that depicts the in-flow of contrast. This application is particularly challenging when imaging coronary arteries or other vessels that require cardiac gating to suppress motion artifacts.

Since the introduction of angiography beginning with the direct carotid artery punctures of Moniz in 1927, there have been ongoing attempts to develop angiographic techniques that provide diagnostic images of the vasculature, while simultaneously reducing the invasiveness associated with the procedure. For decades, post-processing of images was largely limited to the use of film subtraction techniques. Initial angiographic techniques involved direct arterial punctures and the manipulation of a needle through which a contrast medium was injected. These practices were associated with a significant incidence of serious complications. The development of percutaneous techniques allowing the use of a single catheter to study multiple arterial segments reduced, but this by no means eliminated, these adverse events. In the late 1970's, a technique known as digital subtraction angiography (DSA) was developed based on real-time digital processing equipment. Because of the advantages of digital processing, it was originally hoped that DSA could be consistently implemented using an IV injection of contrast medium, thus reducing both the discomfort and the incidence of complications associated with direct IA injections.

However, it quickly became apparent that the IV-DSA technique was limited by problems due to suboptimal viewing angles and vessel overlap that could only be reduced by repeated injections. Even then, these factors were problematic unless a projection that avoided the overlap of relevant vascular structures could be defined. Similar problems occurred when using biplane acquisitions. Also, because of the limited amount of signal associated with the IV injection of contrast medium, IV-DSA was best performed in conditions with adequate cardiac output and minimal patient motion. IV-DSA was consequently replaced by techniques that combined similar digital processing with standard IA angiographic examinations. Nevertheless, because DSA can significantly reduce both the time necessary to perform an angiographic examination and the amount of contrast medium that was required, its availability resulted in a significant reduction in the adverse events associated with angiography. Due to steady advancements in both hardware and software, DSA can now provide exquisite depictions of the vasculature in both 2D and rotational 3D formats. Three-dimensional digital subtraction angiography (3D-DSA) has become an important component in the diagnosis and management of people with a large variety of central nervous system vascular diseases.

Current limitations in the temporal resolution capabilities of x-ray angiographic equipment require that rotational acquisitions be obtained over a minimum time of about 5 seconds. Even with perfect timing of an acquisition so that arterial structures are fully opacified at the onset of a rotation, there is almost always some filling of venous structures by the end of the rotation. Display of a "pure" image of arterial anatomy is only achieved by thresholding such that venous structures, which contain lower concentrations of contrast medium than arterial structures, are no longer apparent in the image. This limitation is a significant factor in making it prohibitively difficult to accurately measure the dimensions of both normal and abnormal vascular structures. Traditional DSA-based techniques do not depict the temporal sequence of filling in a reconstructed 3D-DSA volume.

In recent years competition for traditional DSA has emerged in the form of CT angiography (CTA) and Magnetic Resonance Angiography (MRA). CTA provides high spatial resolution, but is not time-resolved unless the imaging volume is severely limited. CTA is also limited as a standalone diagnostic modality by artifacts caused by bone at the skull base and the contamination of arterial images with opacified venous structures. Further, CTA provides no functionality for guiding or monitoring minimally-invasive endovascular interventions. Significant advances have been made in both the spatial and the temporal resolution qualities of MRA. Currently, gadolinium-enhanced time-resolved MRA (TRICKS) is widely viewed as a dominant clinical standard for time-resolved MRA. TRICKS enables voxel sizes of about 10 mm$^3$ and a temporal resolution of approximately 10 seconds. Advancements such as HYBRID HYPR MRA techniques, which violate the Nyquist theorem by factors approaching 1000, can provide images with sub-millimeter isotropic resolution at frame times just under 1 second. Nonetheless, the spatial and temporal resolution of MRA are not adequate for all imaging situations and its costs are considerable.

Therefore, it would be desirable to have a system and method that improves the available information related to angiography, such as by providing quantitative information.

SUMMARY

In accordance with one aspect of the present disclosure, a method for generating quantitative computed tomography (CT) angiographic images is provided that includes acquiring a set of projection views forming CT angiographic image data of a patient using a projection duration of less than 50 milliseconds. The method also includes producing a composite image from the CT angiographic image data that indicates an attenuation value at each composite image pixel of the patient, backprojecting each projection view in the CT angiographic image data and weighting a value backprojected into at image pixel by an attenuation value of a corresponding pixel in the composite image, and summing backprojected values for each image pixel to produce a CT image of the patient. The method also includes performing a scatter correction on at least one of the CT angiographic image data and the CT image of the patient, determining at least one of a flow direction or a velocity of flow with a vessel in the patient, and displaying the at least one of the flow direction or the velocity of flow with the vessel in the patient with the CT image of the patient to provide the quantitative CT angiographic images.

In accordance with another aspect of the present disclosure, a system is provided for generating quantitative computed tomography (CT) angiographic images. The system includes a rotatable gantry including a radiation source and a detector coupled thereto, wherein the rotatable gantry is configured to receive a patient to rotate the radiation source and the detector around the patient to acquire a set of projection views forming CT angiographic image data of the patient using a projection duration of less than 50 milliseconds. The system also includes a computer system programmed to receive the CT angiographic image data from the detector and generate quantitative CT angiographic images. The computer system is programmed to generate the quantitative CT angiographic images by producing a composite image that indicates an attenuation value at each composite image pixel of the patient and reconstructing the quantitative CT angiographic images of the patient. Reconstruction is performed by backprojecting each projection view in the CT angiographic image data and weighting a value backprojected into at image pixel by an attenuation value of a corresponding pixel in the composite image and summing backprojected values for each image pixel to produce a CT image of the patient. Reconstruction also includes performing a scatter correction on at least one of the CT angiographic image data and the CT image of the patient, determining at least one of a flow direction or a velocity of flow with a vessel in the patient, and combining the at least one of the flow direction or the velocity of flow with the vessel in the patient with the CT image of the patient to generate the quantitative CT angiographic images.

In accordance with yet another aspect of the present disclosure, a method is provided for generating quantitative computed tomography (CT) angiographic images. The method includes acquiring a set of projection views forming CT angiographic image data of a patient using a projection duration of less than 50 milliseconds, producing a composite image from the CT angiographic image data that indicates an attenuation value at each composite image pixel of the patient, and backprojecting each projection view in the CT angiographic image data and weighting a value backprojected into at image pixel by an attenuation value of a corresponding pixel in the composite image. The method also includes summing backprojected values for each image pixel to produce a CT image of the patient and determining at least one of a flow direction or a velocity of flow with a vessel in the patient. The determining is achieved by determining a centerline for the vessel in the patient using the CT image of the patient, generating signal vs. time curves for a plurality of points along the centerline of the vessel, convolving the signal vs. time curves with a temporal kernel to reduce effects of pulsatility, calculating a rising integrated signal (conrise) for a plurality of positions along the vessel in the patient, and calculating a meant transit time (MTT) through the vessel in the patient over an interval selected based on the conrise for each of the plurality of positions. The method then includes displaying the at least one of the flow direction or the velocity of flow with the vessel in the patient with the CT image of the patient to provide the quantitative CT angiographic images.

Various other features of the present invention will be made apparent from the following detailed description and the drawings.

DETAILED DESCRIPTION

Shortcomings of existing angiography methods are particularly prevalent when imaging the small size and convoluted course of the intracranial vasculature. With traditional DSA it is difficult or impossible to image and display these structures without the overlap of adjacent vessels. This problem is compounded when visualizing abnormal structures with complex geometry, such as aneurysms, or when abnormally fast or slow flow is present, such as in vascular malformations or ischemic strokes. As cerebrovascular diseases are increasingly treated using minimally invasive endovascular techniques where a physical is dependent upon imaging techniques for visualization of vascular structures, it is becoming more important to develop imaging methods that allow clear definition of vascular anatomy and flow patterns. Such information is becoming a prerequisite for both pre-treatment planning and the guidance of interventional procedures. For example, the endovascular treatment of vascular disease can require accurate navigation through the small and tortuous vessels of the brain and spinal cord. Currently this involves the use of roadmap that must be "reset" numerous times during a typical procedure. In fact, it is not uncommon to have 15 to 20 resets during a given procedure. Not only does this use large amounts of contrast medium, but the risk of thromboembolic complications increases with each injection.

Even the advent of highly-efficient technologies, such HYPR applied to CT, such as described in U.S. Pat. No. 7,545,901, and 4D DSA, such as described in U.S. Pat. No. 8,643,642, did not provide clinicians with quantitative angiographic information.

HYPR CT

Figure 1A:
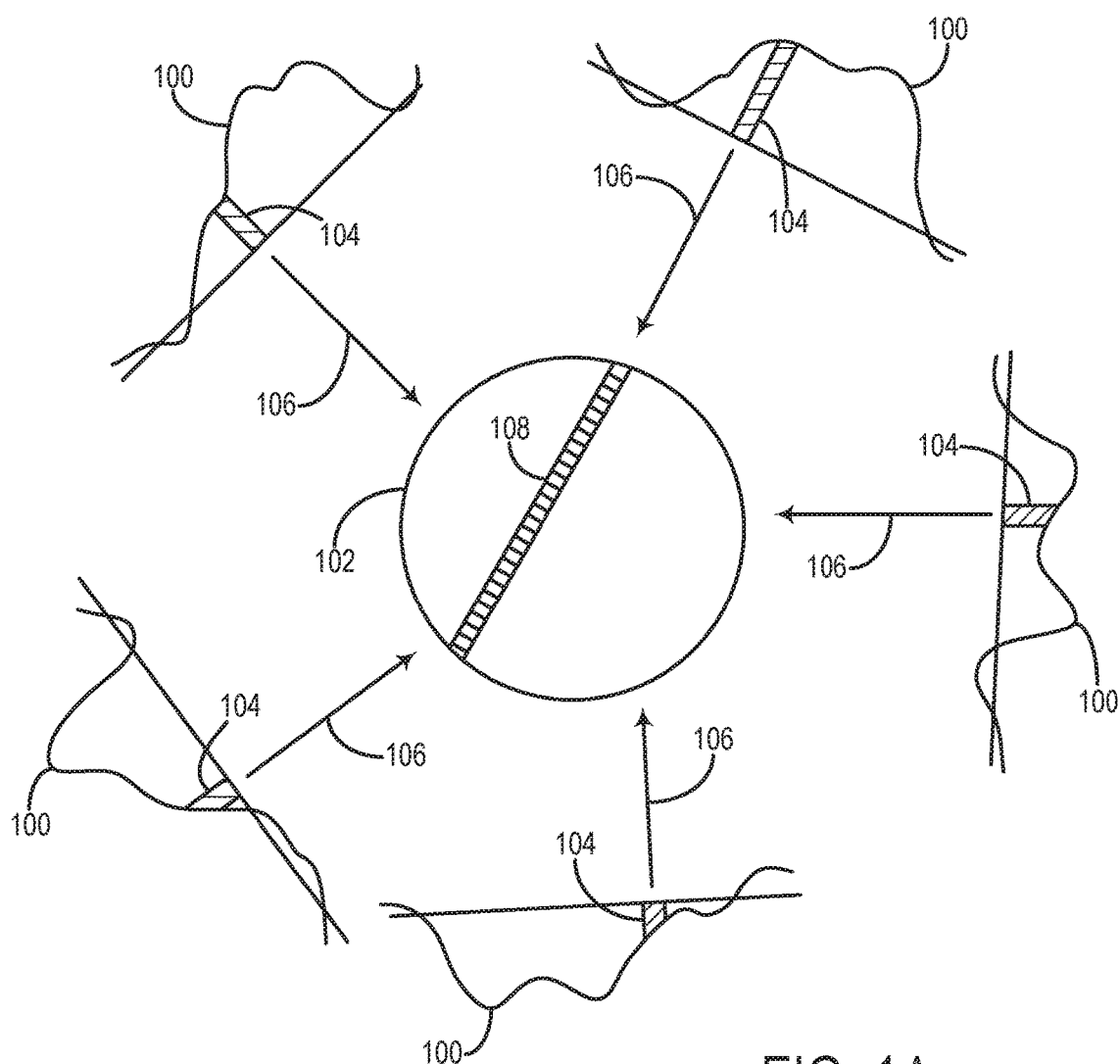
FIG. 1A is a pictorial representation of a conventional backprojection image reconstruction method.
Figure 1B:
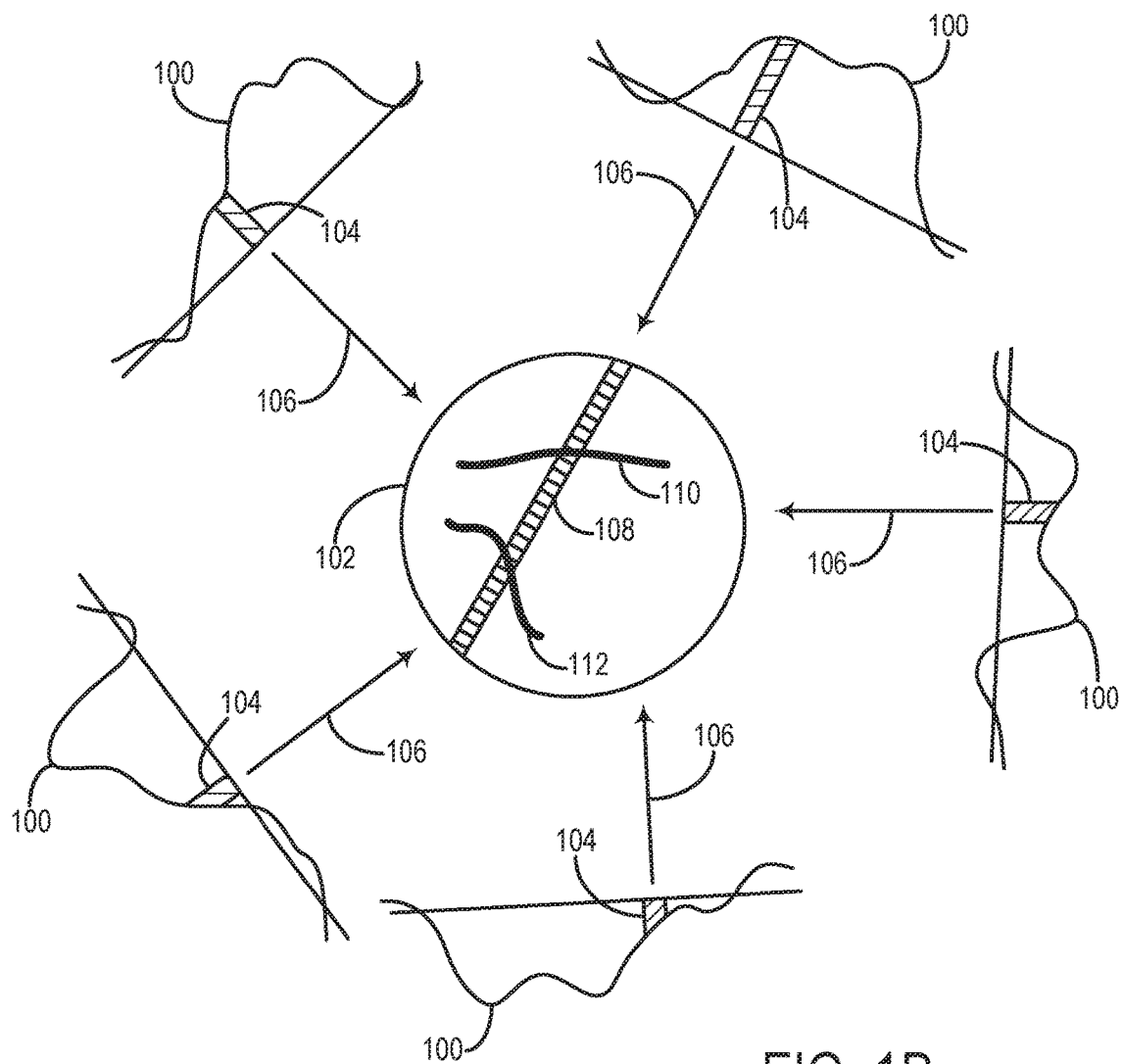
FIG. 1B is a pictorial representation of a conventional backprojection image reconstruction method utilizing HYPR.

In particular, HYPR is built upon the discovery that clinically-usable CT image can be produced with far fewer attenuation profiles than demanded by the Nyquist sampling theorem if a priori knowledge of the x-ray attenuation contour in the FOV 102 of FIG. 1A is used in the backprojection process instead of the assumed homogeneous attenuation contour. Referring to FIG. 1B, for example, the attenuation contour in the FOV 102 may be known to include structures such as blood vessels 110 and 112. That being the case, when the backprojection ray path 108 passes through these structures a more accurate distribution of the ray sum 104 in each ray path pixel is achieved by weighting the distribution as a function of the known attenuation contour at that pixel location. As a result, a majority of the ray sum 104 will be distributed in the example of FIG. 1B at the ray path pixels that intersect the structures 110 and 112. For a backprojection ray path 108 having N pixels this may be expressed as follows:

$$\mu_n = (P \times C_n) / \sum_{n=1}^{N} C_n; \quad (2)$$

where: P=the ray sum attenuation value and $C_n$=attenuation value of an a priori composite image at the $n^{th}$ pixel along the backprojection ray path. The numerator in equation (2) weights each pixel using the corresponding attenuation value in the composite image and the denominator normalizes the value so that all backprojected ray sums are given equal weight by the process.

It should be noted that while the normalization can be performed on each pixel separately after the backprojection, in many clinical applications it is far easier to normalize the ray sum attenuation value P before the backprojection. In this case, the ray sum P is normalized by dividing by the corresponding value $P_C$ in a projection through the composite image at the same view angle. The normalized ray sum $P/P_C$ for each view angle is backprojected and summed to form an unconstrained image, and the resulting unconstrained image is then multiplied by the composite image.

Figure 1C:
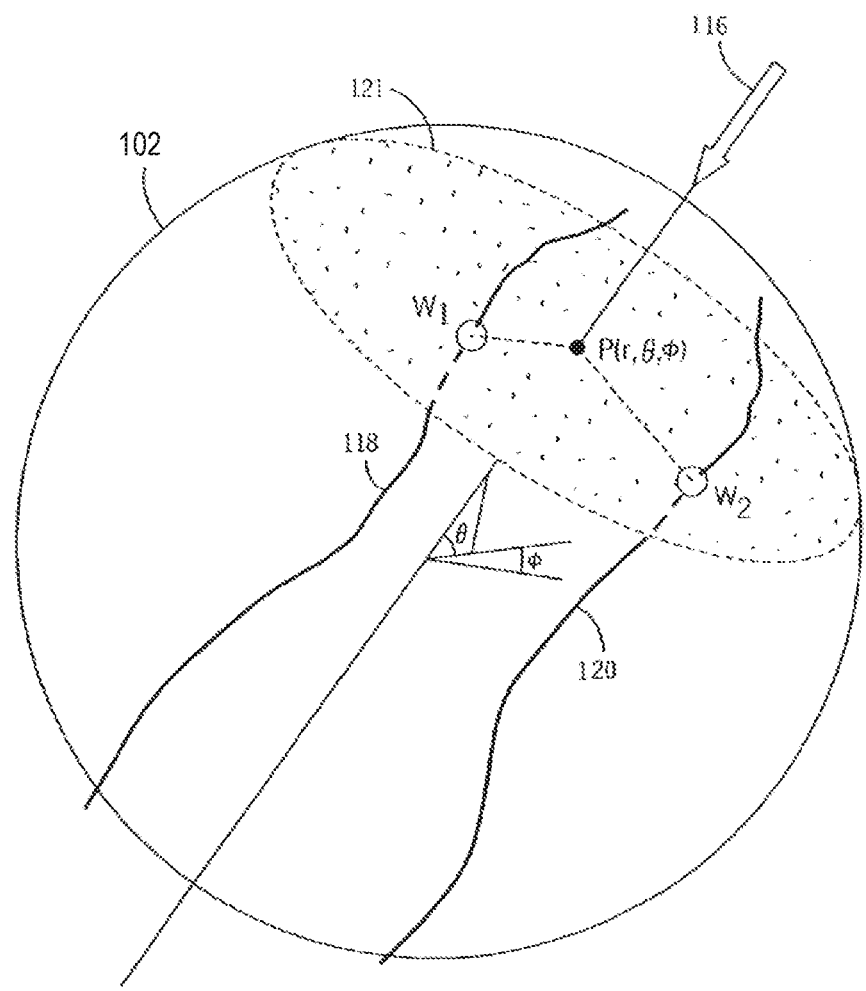
FIG. 1C is a pictorial representation of a 3D backprojection image reconstruction method using HYPR.

A 3D embodiment of the highly constrained backprojection is shown pictorially in FIG. 1C for a single 3D projection view characterized by the view angles θ and φ. This projection view is back projected along axis 116 and spread into a Radon plane 121 at a distance r along the back projection axis 116. Instead of a filtered back projection in which projection signal values are filtered and uniformly distributed into the successive Radon planes, along axis 116, the projection signal values are distributed in the Radon plane 121 using the information in the composite image. The composite image in the example of FIG. 1C contains vessels 118 and 120. The weighted attenuation value is deposited at image location x, y, z in the Radon plane 121 based on the value at the corresponding location x, y, z in the composite image. This is a simple multiplication of the backprojected ray sum value P by the corresponding composite image pixel value. This product is then normalized by dividing the product by the ray sum attenuation value from the corresponding image space projection view of the composite image. The formula for the 3D reconstruction is:

$$I(x,y,z)=\Sigma(P(r,\theta,\phi)*C(x,y,z)_{(r,\theta,\phi)}/P_c(r,\theta,\phi)) \qquad (2a);$$

where the sum ($\Sigma$) is over all projections in the image frame being reconstructed and the x, y, z values in a particular Radon plane are calculated using the projection ray sum value $P(r,\theta,\phi)$ at the appropriate $(r,\theta,\phi)$ value for that plane. $P_C(r,\theta,\phi)$ is the corresponding ray sum attenuation value from the composite image, and $C(x,y,z)_{(r,\theta,\phi)}$ is the composite image value at $(r,\theta,\phi)$.

Figure 2:
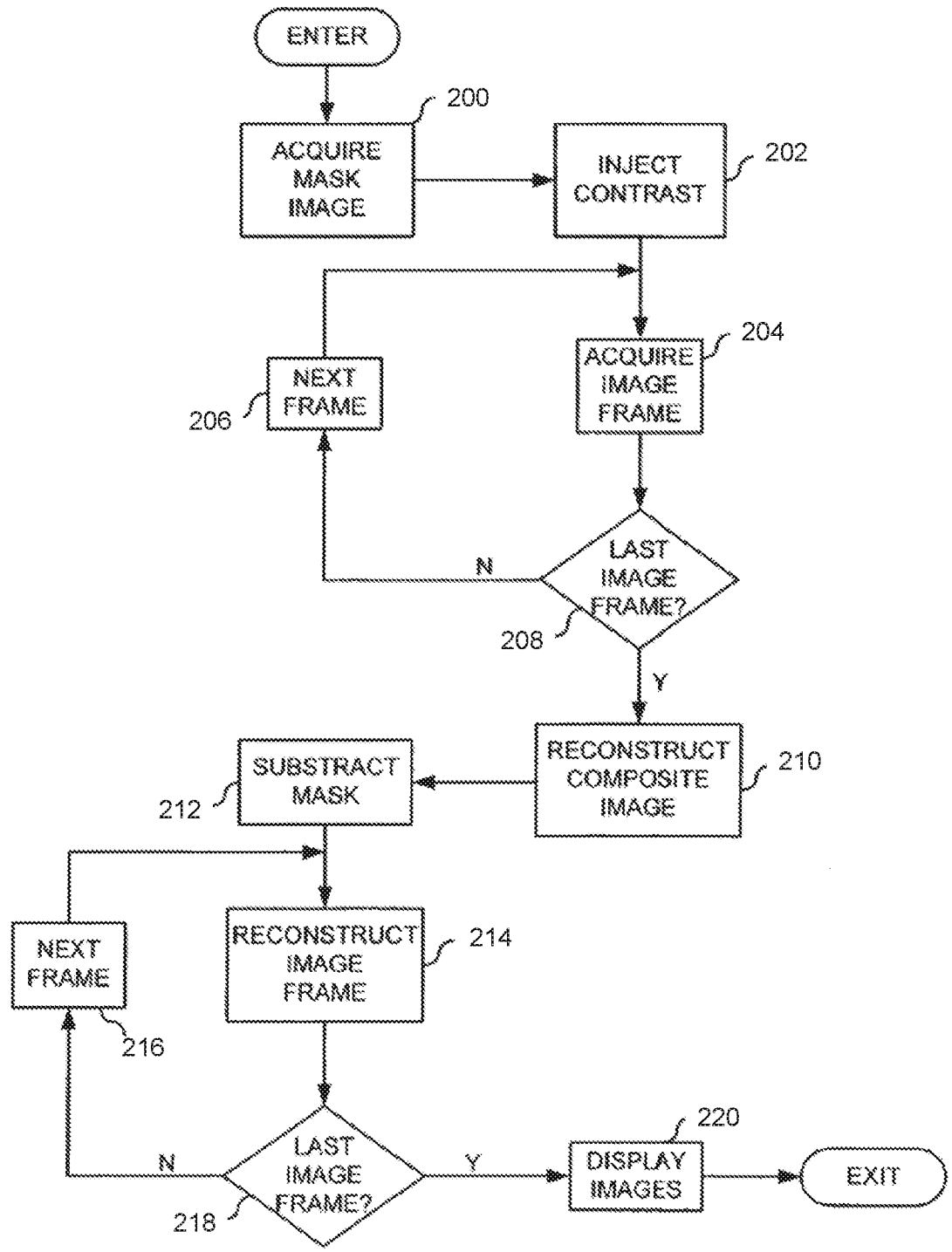
FIG. 2 is a flow chart setting forth some non-limiting example steps of a HYPR process.

Using HYPR, a series of time resolved image frames are acquired when a selected physiological event is occurring in the subject. Referring to FIG. 2, such a process for performing a CT study utilizing HYPR beings, as indicated at process block 200 a mask image is acquired prior to contrast injection. After the mask image is acquired, the contrast agent is injected as indicated at process block 202. A loop is then entered in which a series of frame images are acquired as the contrast agent flows into the region of interest. One cardiac gated image frame is acquired as indicted at process block 204 at the same cardiac phase as the mask image. With the multi-source system, for example, the complete image frame may be acquired in a single 8 msec acquisition and then the sources are rotated to another, interleaved position as indicated at process block 206. When the last image frame has been acquired as indicated at decision block 208, the acquisition phase of the procedure is completed and image reconstruction begins.

Prior to reconstructing the temporally resolved image frames a high resolution composite image is reconstructed as indicated at process block 210. This may be achieved using a conventional filtered backprojection reconstruction of the interleaved projections in all or some of the acquired image frames. Since the image frames are acquired at interleaved view angles, collectively they provide a complete sampling and an artifact-free composite image can be produced using a conventional image reconstruction method. Since the composite image is to be used to reconstruct each image frame, the composite image can be "edited" by subtracting the pre-contrast mask image from it to remove stationary tissues as indicated at process block 212. In addition, to provide a sparse data set for the highly constrained image reconstruction procedure to follow, the individual projection views in each acquired image frame may have the corresponding projection view from the mask image subtracted from it.

The series of time resolved image frames are then reconstructed. A loop is entered in which the limited set of views that comprise an image frame are backprojected using the HYPR method as indicated at process block 214. As will be described, each image frame can be processed as indicated at 216 until the last image frame is reconstructed as determined at decision block 218. The reconstructed image frames may then be displayed as indicated at process block 220. The user may play the entire image frame sequence to observe the inflow of contrast agent into the vasculature of interest or the user may select one or more of the image frames that exhibit the best diagnostic information.

Successive image frames may also be combined to improve image SNR and when 3D image frames are produced, 2D MIP projection images are usually produced from them. As described above the composite image is formed using sets of projections acquired during the dynamic phase of the scan. All or a portion of the sets of acquired projections may be used in forming the composite image, and when the dynamic phase of the scan extends over a longer period of time, this may include one or more sets of projections acquired at the same projection angles. In such case the corresponding values in repeated projection views are averaged to improve SNR.

On the other hand, there are also clinical applications where less than all the acquired sets of interleaved projections are used to reconstruct the composite image. For example, when a contrast agent is employed the subject looks considerably different at different times during the dynamic study. To reflect this change in the subject, more than one composite image may be reconstructed using less than all of the sets of acquired projections so that the composite image is kept up-to-date with the changing subject.

If the frame images are reconstructed after the dynamic scan is completed, the window of acquired image frames used to update the composite image may extend to include image frames acquired after the current image frame. For example, the image frame being reconstructed may be centered in the window with a substantially equal number of other image frames acquired before and after the current image frame. Or, the current image frame may be acquired at the beginning of the window. In this post-processing of the acquired image frames a number of different image frames can be reconstructed in which both the window size and the positioning of the window relative to the current image frame may be varied to achieve the best results.

There are also clinical applications where the composite image may be reconstructed from projections that are acquired prior to the dynamic acquisition phase of the scan. In this case, a high resolution and high SNR composite image is acquired at the beginning of the procedure and reconstructed using a conventional filtered backprojection method. A loop is then entered in which image frames are acquired and displayed. An image frame is acquired with a minimal number of projection views as described above. These projections are aligned, or registered with the composite image to measure translational and rotational motion of the subject. This motion information is used to move the composite image such that it is aligned with the current position of the subject and then the image frame is reconstructed using the registered composite image in the highly constrained backprojection method.

Figure 3:
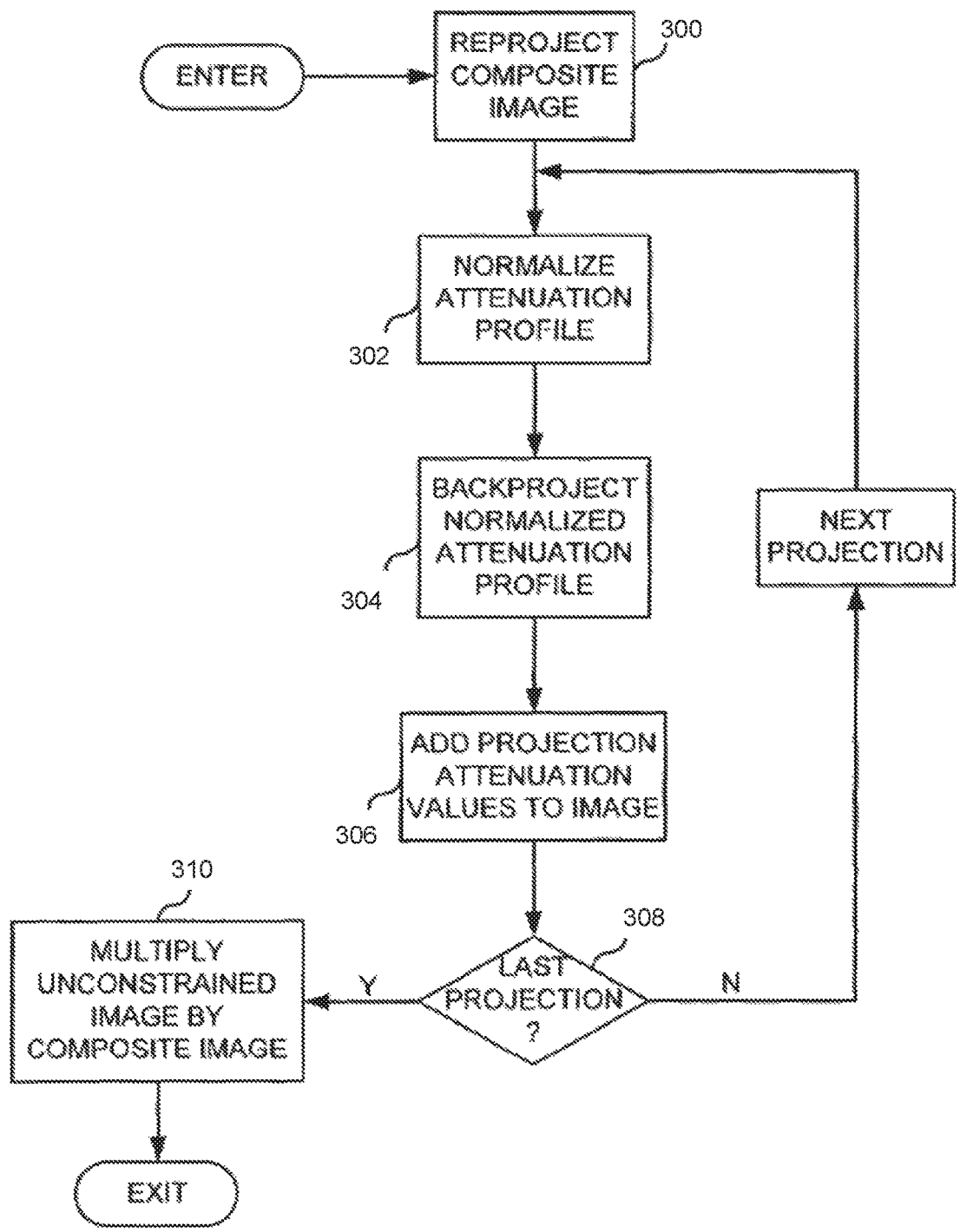
FIG. 3 is a flow chart setting forth some further non-limiting example steps of a HYPR process.

Regardless of the particular acquisition strategies, referring to FIG. 3, a process for HYPR-based CT reconstruction is illustrated. While there are a number of different ways to reconstruct an image frame using HYPR, the process may begin at process block 300 with the re-projection of the composite image. For every attenuation profile P in the current image frame a corresponding composite image attenuation profile $P_c$ is calculated at the same view angle. This re-projection of the composite image is a Radon transformation.

A loop is then entered in which each image frame attenuation profile is normalized at process block 302, backprojected at process block 304, and summed with an unconstrained image frame at process block 306. More specifically, an image frame attenuation profile may be normalized by dividing each attenuation ray sum P by the corresponding attenuation ray sum $P_C$ in the composite image reprojection at the same view angle. This normalized attenuation profile may then be backprojected without any filtering. The resulting unconstrained image values are summed with those back projected from the other attenuation profiles for the current image frame.

When the last attenuation profile has been processed for the current image frame as determined at decision block 308, the reconstructed unconstrained image frame is constrained using the composite image as indicated at process block 310. This is a matrix multiplication in which pixels in the unconstrained image frame are multiplied by the value of corresponding pixels in the composite image. In contrast to prior image reconstruction methods, far fewer projections are needed when the reconstruction method of the present invention is used, and thus, an image frame can be produced very quickly. Image artifacts due to undersampling are suppressed and the higher SNR of the composite image is conveyed to the reconstructed image frame.

The above-described processes may be adapted for other angiographic procedures, including perfusion studies and the like. In particular, referring to FIG. 4, initial rotations are performed to acquire a pre-injection mask as indicated at process block 400. This mask image may be acquired at full x-ray dose. After the pre-injection mask data is obtained, a contrast agent is administered as indicated at process block 402. The contrast agent can be injected through typical arterial injection, but may also include intravenously introduction.

As indicated at process block 404, a series of image frames are then acquired at a low dose. This may be achieved by rotating the gantry and acquiring a reduced number of projection views during the revolution. For example, whereas 400 projection views might be acquired during a normal scan, a substantially reduced number of projection reviews, such as only 40 projection views, may be acquired during this low-dose acquisition. As determined at decision block 408, this is repeated as indicated at process block 406 until all of the desired image frames are acquired.

In this non-limiting example, of each image frame being comprised of 40 views, the x-ray dose which the subject receives is only one-tenth the x-ray dose that would be received if a fully sampled image (e.g., 400 views) were acquired for each image frame. Alternatively, each image frame may be acquired as a full set of 400 projection views. However, in this approach a lower x-ray dose is delivered to the subject by reducing the intensity of the x-ray beam produced by the x-ray source. This is achieved by, for example, reducing the x-ray tube current. Of course, by reducing the x-ray beam strength in this manner one would expect the SNR of the resulting reconstructed image to be reduced by a corresponding amount. By performing a highly constrained backprojection as described below, however, the lost SNR is recaptured.

After the image frames are acquired using either of the above-described low dose methods, the acquired mask projection views are subtracted as indicated at process block 410. This is a subtraction from attenuation values in each acquired image frame projection view of corresponding attenuation values in the mask image projection acquired at the same view angle. The resulting image frame projection views indicate the difference in x-ray attenuation caused by perfusion of the contrast agent into the tissues being examined.

Prior to reconstructing the perfusion images a high resolution composite image is reconstructed as indicated at process block 412. This is a filtered backprojection reconstruction using the difference projection views from all of the acquired image frames. Since the image frames are acquired at interleaved view angles in the first embodiment, collectively they provide a complete sampling of Radon space and an artifact-free, high SNR composite image can be produced with a standard reconstruction method. In the second approach described above the corresponding low-dose views acquired for each image frame are averaged to provide a higher SNR composite image than would otherwise be produced from one complete set of low dose views.

The series of time resolved perfusion image frames are then reconstructed and displayed. A loop is entered in which the limited set of difference views that comprise an image frame are backprojected using the highly constrained method described above and shown in FIG. 9 as indicated at process block 414. Each perfusion image frame is reconstructed as indicated at 416 until the last perfusion image frame is reconstructed as determined at decision block 418. The reconstructed perfusion image frames may then be displayed as indicated at process block 420 or further processed to provide images indicative of tissue health.

4D DSA

As described in U.S. Pat. No. 8,643,642, the generation of 4D DSA images is accomplished using a constrained reconstruction technique in which two acquisitions are performed, one with and one without contrast injection. As will be described, the two acquisitions are traditionally performed using two C-arm sweeps; however, in accordance with the present disclosure, traditional CT imaging systems may be used.

Figure 4:
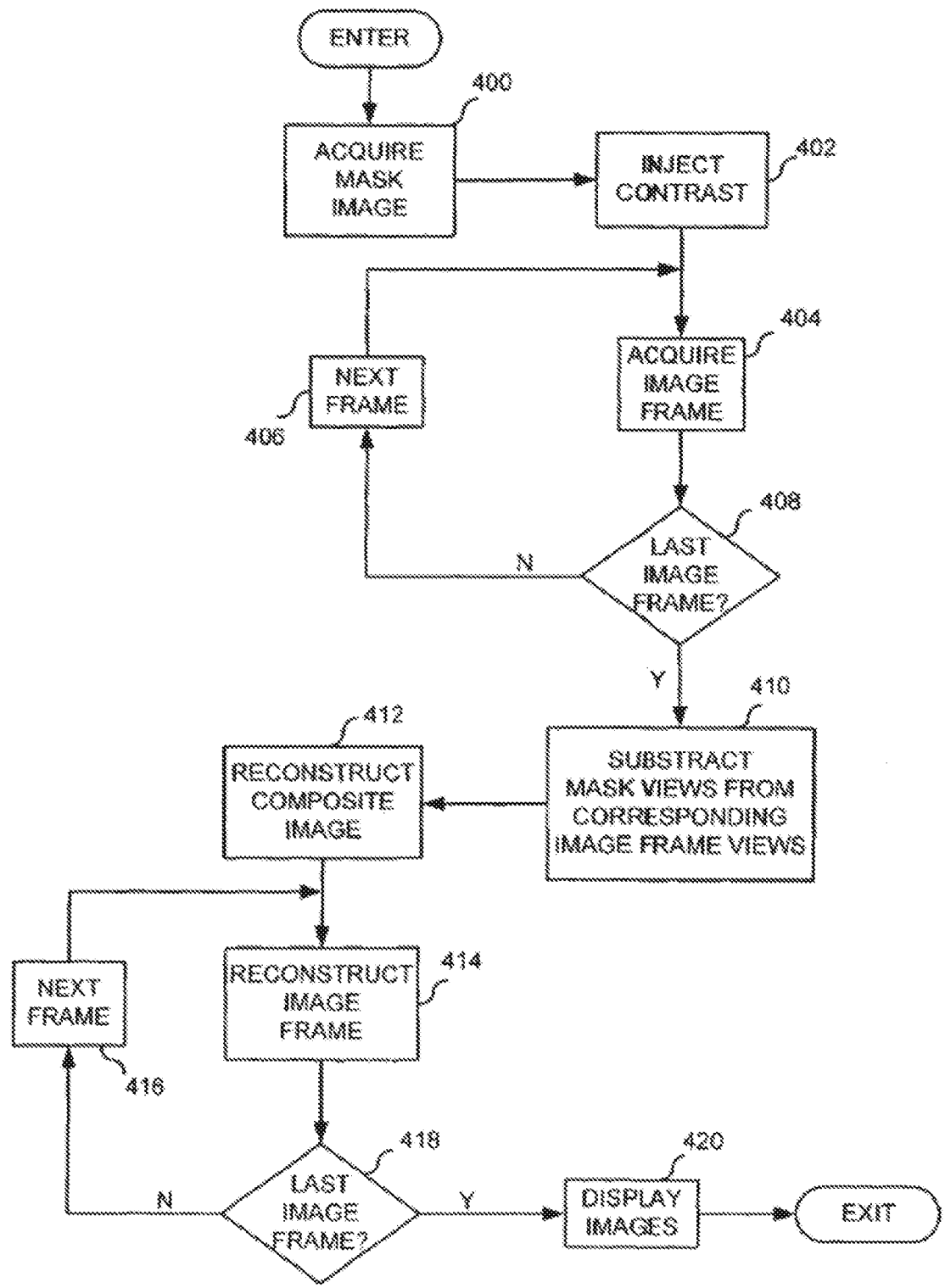
FIG. 4 is a flow chart setting forth some non-limiting example steps of a HYPR process employed to perform a CT angiographic study.
Figure 5A:
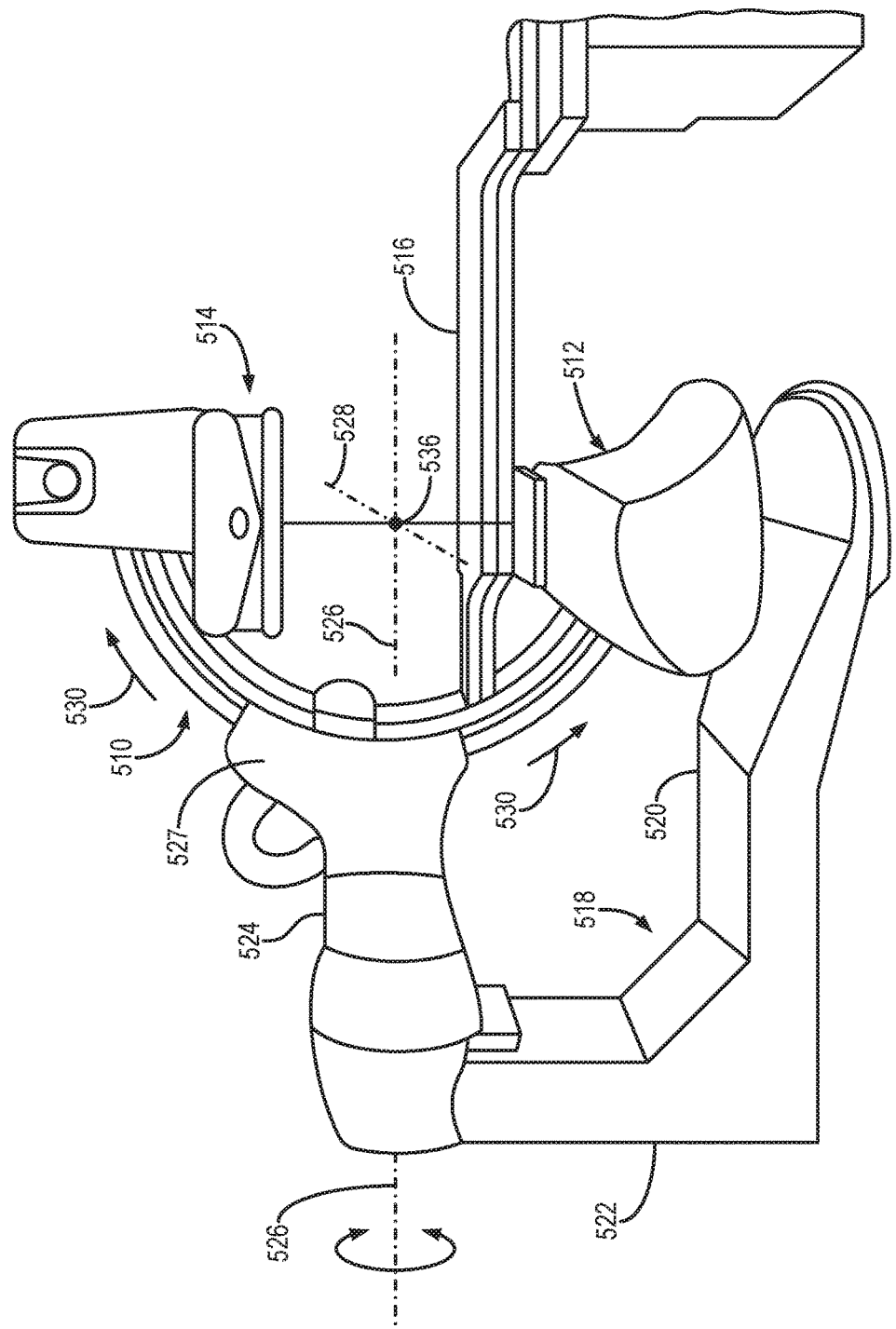
FIG. 5A is a perspective view of a rotational, C-arm x-ray system configured to carry out a 4D DSA process.

That is, referring to FIG. 5A, 4D DSA often employs a rotational x-ray system that is designed specifically for use in connection with interventional procedures. It is characterized by a gantry having a C-arm 510 which carries an x-ray source assembly 512 on one of its ends and an x-ray detector array assembly 514 at its other end. The gantry enables the x-ray source 512 and detector 514 to be oriented in different positions and angles around a patient disposed on a table 516, while enabling a physician access to the patient.

The gantry includes an L-shaped pedestal 518 which has a horizontal leg 520 that extends beneath the table 516 and a vertical leg 522 that extends upward at the end of the horizontal leg 520 that is spaced from of the table 516. A support arm 524 is rotatably fastened to the upper end of vertical leg 522 for rotation about a horizontal pivot axis 526. The pivot axis 526 is aligned with the centerline of the table 516 and the arm 524 extends radially outward from the pivot axis 526 to support a C-arm drive assembly 527 on its outer end. The C-arm 510 is slidably fastened to the drive assembly 527 and is coupled to a drive motor (not shown) which slides the C-arm 510 to revolve it about a C-axis 528 as indicated by arrows 530. The pivot axis 526 and C-axis 528 intersect each other at an isocenter 536 located above the table 516 and they are perpendicular to each other.

The x-ray source assembly 512 is mounted to one end of the C-arm 510 and the detector array assembly 514 is mounted to its other end. The x-ray source 512 emits a beam of x-rays which are directed at the detector array 514. Both assemblies 512 and 514 extend radially inward to the pivot axis 526 such that the center ray of this beam passes through the system isocenter 536. The center ray of the beam can thus be rotated about the system isocenter around either the pivot axis 526 or the C-axis 528, or both during the acquisition of x-ray attenuation data from a subject placed on the table 516.

The x-ray source assembly 512 contains an x-ray source which emits a beam of x-rays when energized. The center ray passes through the system isocenter 536 and impinges on a two-dimensional flat panel digital detector housed in the detector assembly 514. The detector 538 may, for example, be a 2048 by 2048 element two-dimensional array of detector elements having a size of 41 cm by 41 cm. Each element produces an electrical signal that represents the intensity of an impinging x-ray and hence the attenuation of the x-ray as it passes through the patient. During a scan the x-ray source assembly 512 and detector array assembly 514 are rotated about the system isocenter 536 to acquire x-ray attenuation projection data from different angles. The detector array is able to acquire 530 projections, or views, per second and this can be the limiting factor that determines how many views can be acquired for a prescribed scan path and speed.

Figure 5B:
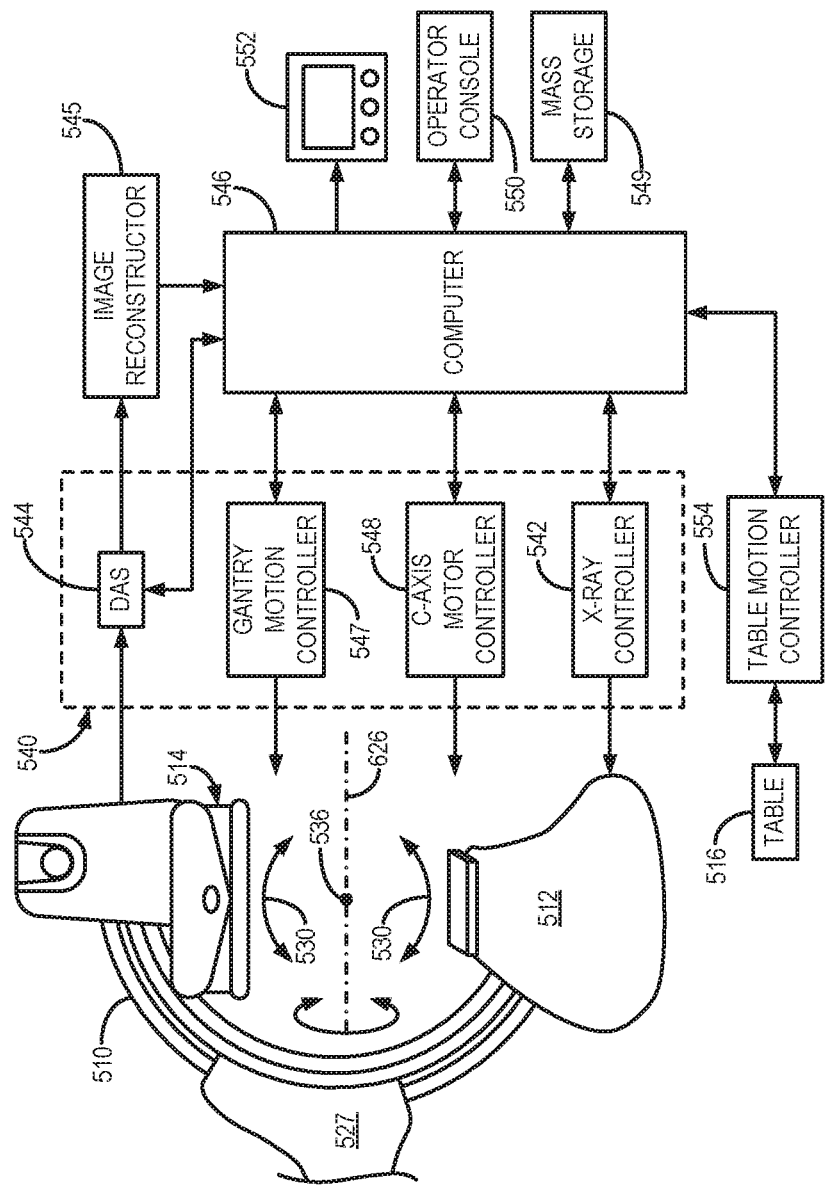
FIG. 5B is a schematic view of the C-arm x-ray system of FIG. 5A.

Referring particularly to FIG. 5B, the rotation of the assemblies 512 and 514 and the operation of the x-ray source are governed by a control system 540 of the x-ray system. The control system 540 includes an x-ray controller 542 that provides power and timing signals to the x-ray source 532. A data acquisition system (DAS) 544 in the control system 540 samples data from detector elements 538 and passes the data to an image reconstructor 545. The image reconstructor 545, receives digitized x-ray data from the DAS 544 and performs high speed image reconstruction according to the methods of the present invention. The reconstructed image is applied as an input to a computer 546 which stores the image in a mass storage device 549 or processes the image further to produce parametric images according to the teachings of the present invention. It is contemplated that the computer 546 may be or include components of a digital vascular image processor (DVIP) system.

The control system 540 also includes gantry motor controller 547 and a C-axis motor controller 548. In response to motion commands from the computer 546 the motor controllers 547 and 548 provide power to motors in the x-ray system that produce the rotations about respective pivot axis 526 and C-axis 528. As will be discussed below, a program executed by the computer 546 generates motion commands to the motor drives 547 and 548 to move the assemblies 512 and 514 in a prescribed scan path.

The computer 546 also receives commands and scanning parameters from an operator via console 550 that has a keyboard and other manually operable controls. An associated cathode ray tube display 552 allows the operator to observe the reconstructed image and other data from the computer 546. The operator supplied commands are used by the computer 546 under the direction of stored programs to provide control signals and information to the DAS 544, the x-ray controller 542 and the motor controllers 547 and 548. In addition, the computer 546 operates a table motor controller 554 which controls the motorized table 516 to position the patient with respect to the system isocenter 536.

Whereas conventional reconstruction methods generally necessitate the acquisition of a minimum number of projections dictated by the Nyquist theorem, the present invention provides a fundamentally new method for imparting temporal resolution from a time-series of 2D images into 3D image volumes to create time-resolved 3D medical images. This allows, among other things, the production of 3D angiograms with both exquisite detail and high temporal resolution. The method can be implemented using a wide-variety of medical imaging systems, such as CT systems, fluoroscopy systems, and the above-discussed rotational x-ray system, either alone or in combination. Accordingly, the present description first presents a generalized method for producing time-resolved 3D images before proceeding to more specific implementations and extensions of the method.

Figure 6:
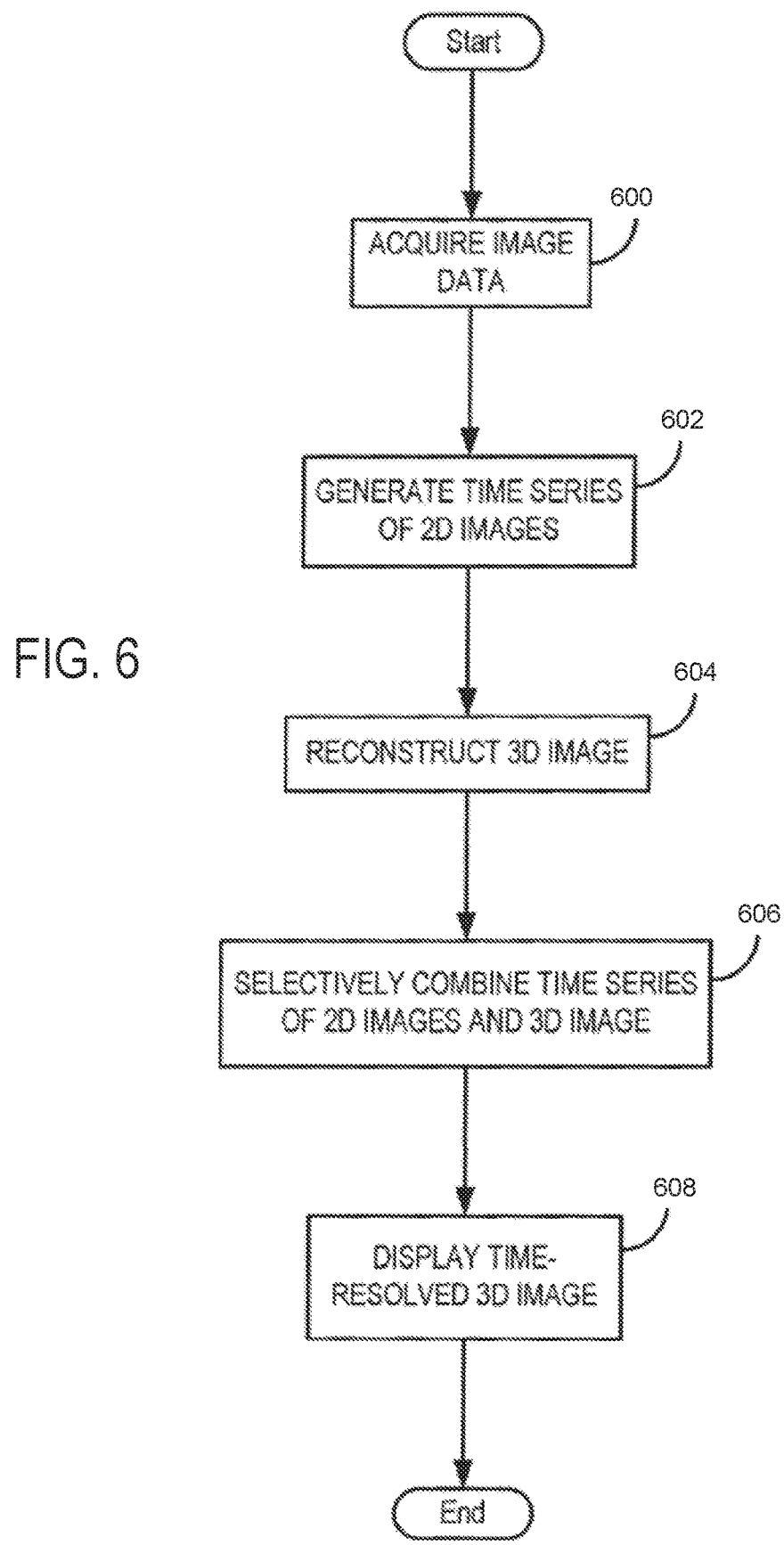
FIG. 6 is a flowchart setting forth the general steps for producing a time-resolved 3D image in accordance with a 4D-DSA process.

Referring now to FIG. 6, a general method for producing a time-resolved 3D image begins at process block 600 with the acquisition of image data from a region-of-interest in a subject using a medical imaging system, such as a CT system or a single-plane, biplane, or rotational x-ray systems. At process block 602, a time-series of 2D images is generated from at least a portion of the acquired image data. While the time-series of 2D images can have a high temporal and spatial resolution and may include images acquired at different angles around the subject, it generally cannot provide a sophisticated 3D depiction of the subject. The production of the time-series of 2D images may be convolved with a convolution kernel in order to provide local spatial coverage with a desired weighting. For example, these weighted images can provide information detailing how much of a vessel tree is present at a given time. It is contemplated that this process can increase SNR by a factor of three over that provided by the original time series pixels when using a 3×3 convolution kernel. At process block 604, a 3D image of the subject is reconstructed from the acquired image data. Though individual projections used to reconstruct this 3D image may themselves convey some degree of temporal information, the reconstructed 3D image itself is substantially free of temporal resolution. For brevity, the 3D image substantially without temporal resolution and the time-series of 2D images may simply be referred to as the "3D image" and "2D images," respectively. It should be noted that the acquisition and reconstruction of the above sets of image data can be performed in accordance with constrained reconstruction techniques, such as highly constrained backprojection reconstruction (HYPR), to improve SNR and permit potential radiation and contrast agent dose reductions.

At process block 606, the time-series of 2D images and the static 3D image are selectively combined so that the temporal information included in the 2D images is imparted into the 3D image. This results in the production of a time-resolved 3D image of the subject with high temporal and spatial resolution. While the selective combination process varies based on the medical imaging system used and the nature of the acquired image data, it generally involves the steps of (1) registering the 2D images to the 3D image, (2) projecting the attenuation value of the pixels in the 2D images into the 3D image, and (3) weighting the 3D image with the projected values for each individual frame of the time-series of 2D images. It is contemplated that the temporal weighting in step (3) generally involves multiplying the projected pixel values with the 3D image. These three steps, which can be referred to as "multiplicative projection processing" (MPP), may be accompanied by additional steps to improve image quality or reduce the prevalence of errors and artifacts. For example, the intensity values of pixels and voxels in the 2D images and 3D image produced at process blocks 602 and 604 may quantify an x-ray attenuation level at a given location in the subject. These attenuation levels may not be preserved when multiplying the 3D image with projected pixel values. Accordingly, more accurate indications of the attenuation levels may be restored by taking a root of the intensity value at each voxel in the time-resolved 3D image, for example, by taking the n-th root if (n−1) different sets of 2D images are used to weight the 3D image. Other processing steps can be performed before the time-resolved 3D image is displayed at process block 608.

The 2D images and 3D image produced at process blocks 602 and 604, respectively, can be produced using DSA techniques. That is, 2D images depicting the subject's vasculature can be produced by reconstructing image data acquired as a bolus of contrast passes through the ROI and subtracting out a pre-contrast, or "mask," image acquired before the administration of contrast agent. Likewise, a 3D image of the same vasculature can be produced by reconstructing image data acquired as contrast agent occupies the ROI and subtracting out a mask image to remove signal associated with non-vascular structures. As will be discussed below, depending on the imaging situation, the time series of 2D-DSA images and the 3D-DSA images can be produced from image data acquired using a single medical imaging system and contrast agent injection or from different sets of image data acquired separately using different medical imaging systems and contrast agent injections. In either case, the time-resolved 3D image produced by combining the DSA images depicts the subject's vasculature with both excellent spatial and excellent temporal resolution and may thus be referred to as a 4D-DSA image. In additional, the 4D-DSA images can be displayed as "pure" arterial, pure venous, or composite arterial and venous images and can be fully rotated during each state of the filling of the vasculature, thereby enabling greatly simplified interpretation of vascular dynamics. The spatial resolution of these 4D-DSA images is generally on the order of $512^3$ pixels at about 30 frames per second. This represents an increase over traditional 3D-DSA frame rates by a factor between 150 and 600, without any significant image quality penalty being incurred.

The acquisition of contrast enhanced image data can be performed following the administration of contrast agent to the subject via either IV or IA injection. When scanning a local area, IA injections allow high image quality and temporal resolution as well as reduced contrast agent dose. However, IV injections are often more suitable for scanning larger regions where multiple IA injections at different locations and different arteries would otherwise be required. For example, there are many clinical cases where multiple 3D-DSA acquisitions, each using a different IA injection, are performed to produce separate studies that can be merged into a larger high quality vascular tree. While separate IA acquisitions may be employed for generating the time-series of 2D images used by the present invention for temporal weighting, the use of an intravenous injection for this purpose provides a mechanism for simultaneously synchronized imparting temporal information to all of the previously acquired anatomical locations present in instances when there are multiple, separate, IA 3D-DSA studies. This process reduces the likelihood of complications associated with IA contrast agent injections and improves scan efficiency. Further, there is filling of arteries and veins with the same concentration of contrast medium in scans performed using IV rather than an IA contrast agent injections, thus allowing the visualization of venous and arterial structures at the same threshold.

Figure 7:
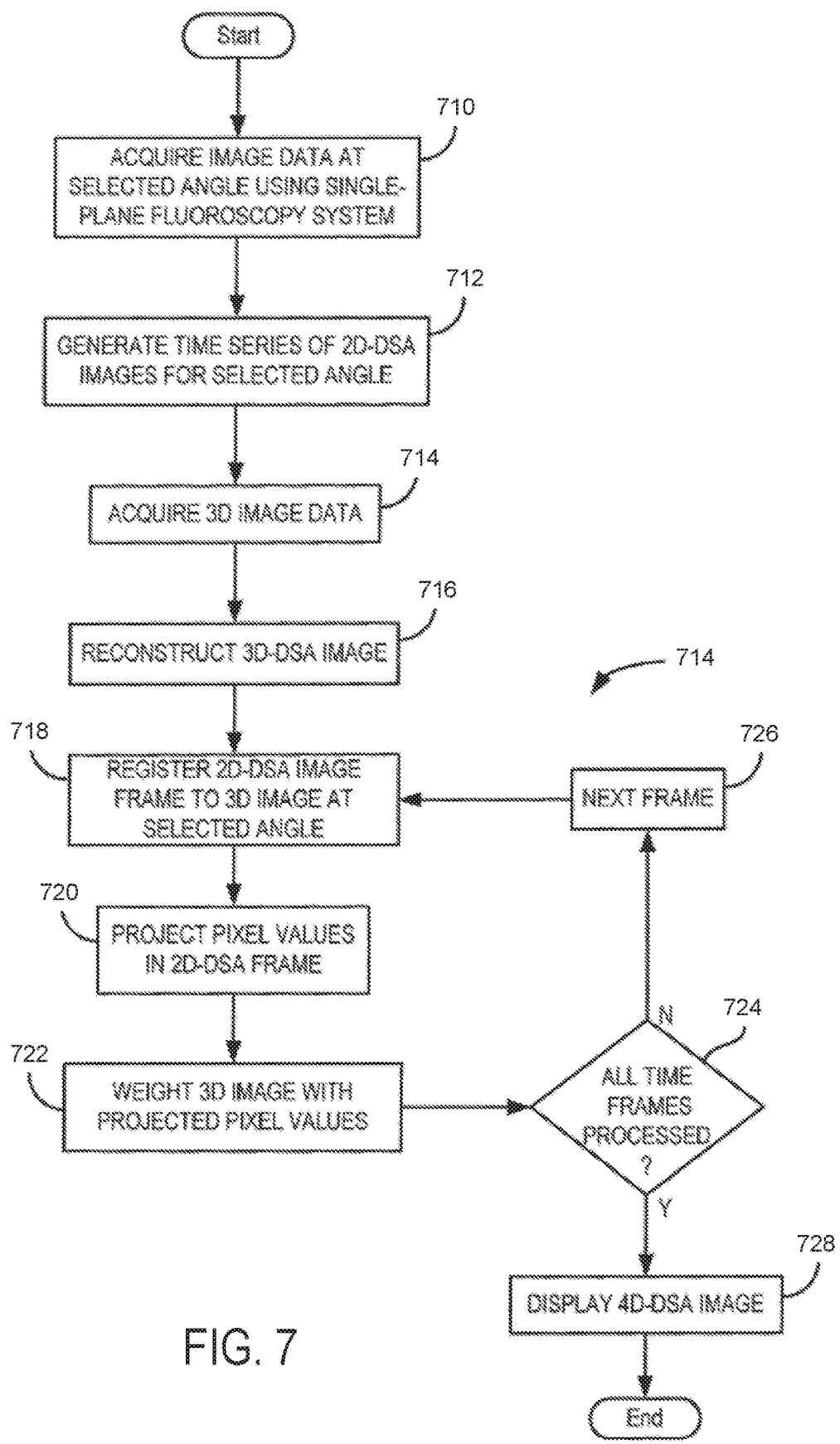
FIG. 7 is a flowchart setting forth the steps for producing a 4D-DSA image from time-resolved 2D images acquired using a single plane x-ray system.

Referring to FIG. 7, a more specific implementation of the above method can be employed to produce a 4D-DSA image of a subject using a single-plane x-ray system in combination with a rotational x-ray system or CT system. This particular method begins at process block 710, when time-resolved image data from a ROI in the subject is acquired using the single-plane system following the administration of a contrast agent to the subject. Using the above-discussed DSA techniques, a time-series of 2D-DSA images at the selected angle is generated at process block 712. These 2D-DSA images depict the contrast agent passing through and enhancing arterial structures in the ROI. The 2D-DSA images are substantially free of signal from non-vascular structures, as well as signal from venous structures can be excluded due to the high temporal resolution of the 2D acquisition. At process 714, a separate scan is performed following a second administration of contrast agent to the subject using either the rotational fluoroscopy system or CT system to acquire 3D image data from the ROI. A 3D-DSA image is reconstructed at process block 716 from the acquired 3D image data. Typically, vascular structures in the 3D-DSA image are substantially opacified due to the use of contrast agent and the time necessary for data acquisition.

Figure 8:
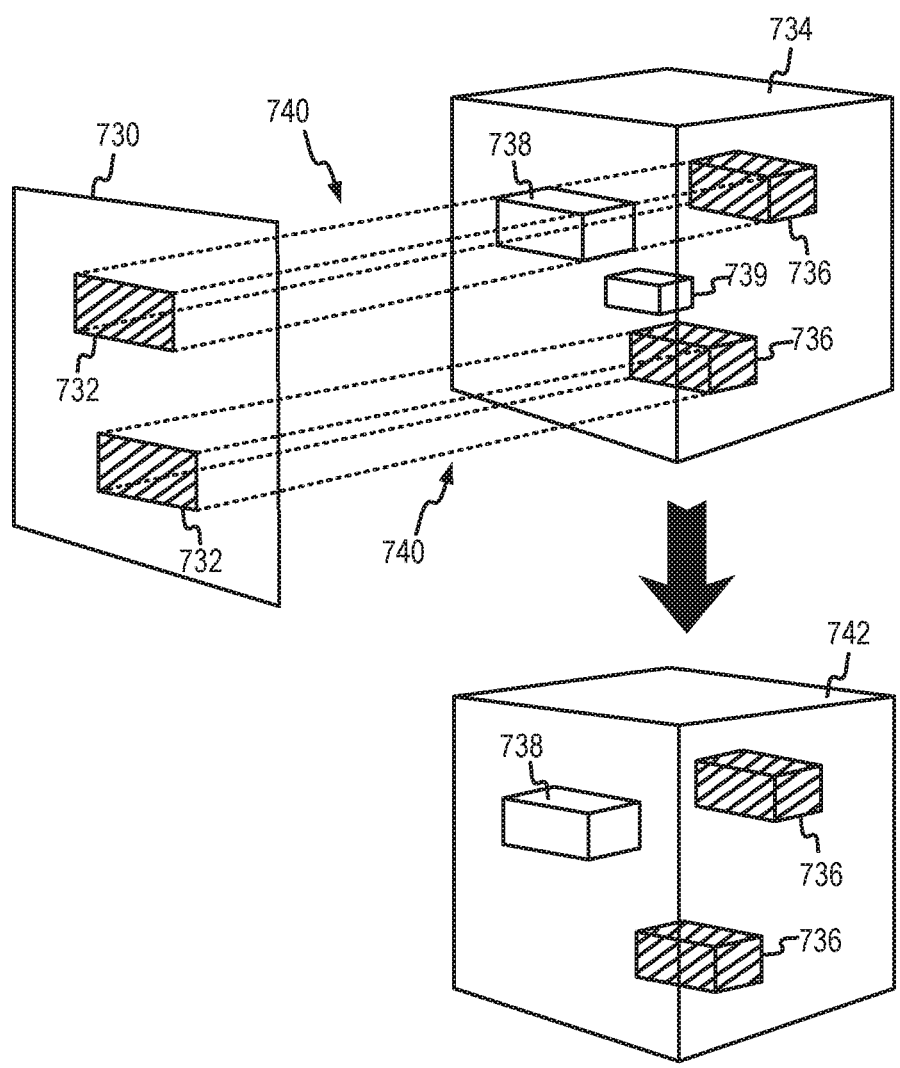
FIG. 8 schematically depicts the selective combination of a 3D image with a 2D-DSA image frame acquired using a single plane x-ray system in accordance with the present invention.

Referring now to FIGS. 3 and 4, the images produced thus far can now be selectively combined with the steps indicated generally at 717 to produce a 4D-DSA image with the detailed 3D resolution of the 3D-DSA image and the temporal resolution of the time-series of 2D-DSA images. In the exemplary depiction of the selective combination process provided in FIG. 8, a single frame of the time-series of 2D-DSA images 730 includes two image regions having arterial signal 732, while the 3D-DSA image 734 includes both arterial signal 736 and venous signal 738 and 739. At process block 718, a frame of the 2D-DSA image 730 is registered to the 3D-DSA image 732 at the selected angle and, at process block 720, the values of the pixels in the 2D-DSA frame are projected along a line passing through each respective pixel in a direction perpendicular to the plane of the 2D-DSA frame. The projection of pixels with arterial signal 732 into the 3D-DSA image is indicated generally at 740. For simplicity, the projection of pixels in the 2D-DSA frame with no contrast is not shown. At process block 722, the 3D-DSA image 734 is weighted by the values projected from the 2D-DSA frame 730 to produce the 4D-DSA image 742. Typically, this includes multiplying the projected values with the voxels of the 3D image that they intersect. The weighting process results in the preservation of the arterial signal 736 and the exclusion, or "zeroing-out," of undesired venous signal 739 in the 4D-DSA image. In addition, the intensity value of the arterial signal 732 in the 2D-DSA frame is imparted into the 3D arterial signal volume 736, thereby allowing the changes in arterial signal over time captured by the 2D-DSA images to be characterized in the 4D-DSA image. At decision block 724, if all of the frames have yet to be processed, the process moves to the next frame of the time-series of 2D-DSA images at process block 726 and repeats the selective combination process 717. This cycle continues until, at decision block 726, it is determined that a 4D-DSA image has been generated for all relevant time frames. The 4D-DSA image can thus be displayed at process block 728.

The venous signal 738 preserved in the 4D-DSA image 742 illustrates a potential problem when generating 4D images using only a single time-series of 2D images acquired at a single angle. Signal from desired structures, such as the arterial signal 732, can inadvertently be deposited in 3D voxels representing undesired structures, such as the venous region 738. The unwanted structures can thus be preserved in the 4D image as "shadow artifacts" when their signal lies along the projected values of a desired structure in a dimension inadequately characterized by the time-series of 2D images. This can result, for example, in a 4D-DSA image in which desired arterial structures are obscured by undesired venous structures for some time frames. However, this will cause a temporary anomaly in the contrast vs. time course for the vein. If the time frames of the 4D-DSA image are analyzed, this anomaly can be recognized as inconsistent with the general waveform of the vein and the vein can be suppressed in the time frame where the projected arterial signal is strong. Accordingly, temporal parameters such as mean transit time (MTT) or time-to-fractional-peak can be calculated for each voxel and this information can be used to clean up shadow artifacts. To assist an operator in identifying shadow artifacts and temporal irregularities, the temporal parameters can be color-coded and superimposed on the 4D-DSA image displayed at process block 728. The temporal parameters can also be exploited to infer information related to potential diffusion abnormalities in the absence of direct perfusion information from parenchymal signal.

The above-described single-plane method may be extended to bi-plane implementations. In this regard, the method for producing 4D-DSA images is less prone to shadow artifacts because the image data is acquired at a first angle (first plane) and an orthogonal second angle using, for example, a biplane fluoroscopy system. Further description of such implementation is described in U.S. Pat. No. 8,643,642, which is incorporated herein by reference. Also, while the above-described methods for generating 4D-DSA images can involve two separate scans using two separate imaging systems and contrast agent injections, the method described with respect to FIG. 6 can be performed on a single medical imaging system using a single contrast agent injection. Further description of such implementation is also described in U.S. Pat. No. 8,643,642.

In the implementations described above, a constraining image is formed from all projections acquired typically in a 5-10 second time period. As described above, the acquisition of angular projections is begun during the injection of contrast so that the projections depict the inflow of contrast to the vessels. Typically, these projections are acquired at 30 frames per second.

The time-dependent projections are back-projected through the constraining vascular volume and the intensity of the projections is deposited only in the non-zero voxels of the constraining volume. In this way, a new 3D vascular volume is generated every 1/30 seconds.

From the signal curves at each point in the vascular tree made available by this time series of images one can estimate blood velocity and flow everywhere in the vascular tree. These have been described in terms of 4D DSA as implemented using slow C-arm rotations of 5-10 seconds.

As will now be described, the present disclosure provides systems and methods to accomplish velocity and flow measurements using computed tomography system. As described, the above described systems and methods may be utilized to perform CT angiography (CTA) using a gantry-based CT system to deliver angiographic images with quantitative information, including flow or velocity information. As will be described, gantry-based CT systems can achieve full CT images at rates on the order of 3 per second. Each volume is acquired using about 300 projections. So, for a 0.3 second acquisition, the projection duration is about 1 millisecond. Generally, such gantry-based CT systems can provide projection duration of less than 50 milliseconds, can be less than 10 milliseconds, and, in a variety of cases, the projection duration can readily be less than or about 1 millisecond. However, to take advantage of such systems, various challenges must be overcome, which are provided herein.

Figure 9A:
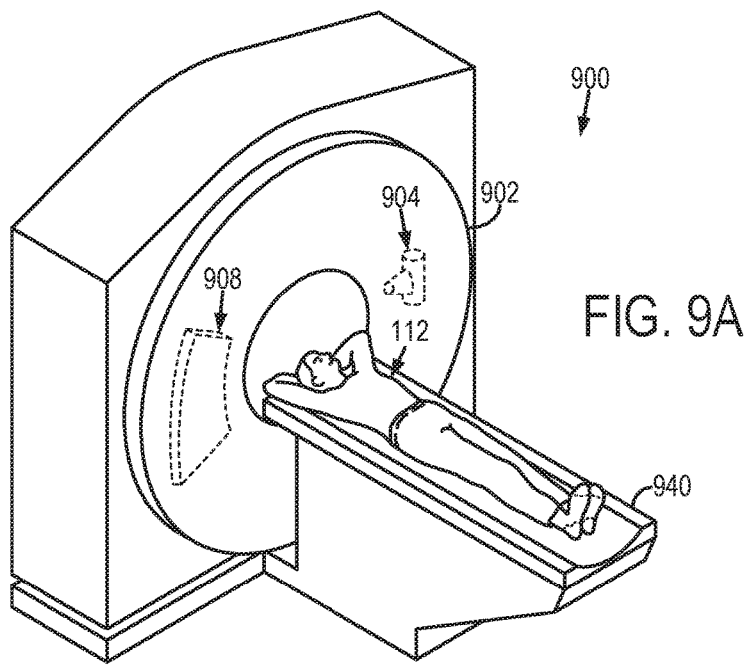
FIG. 9A is a perspective view of a gantry-based CT system that, in accordance with the present disclosure, can be utilized to perform ultrafast quantitative CT angiography.
Figure 9B:
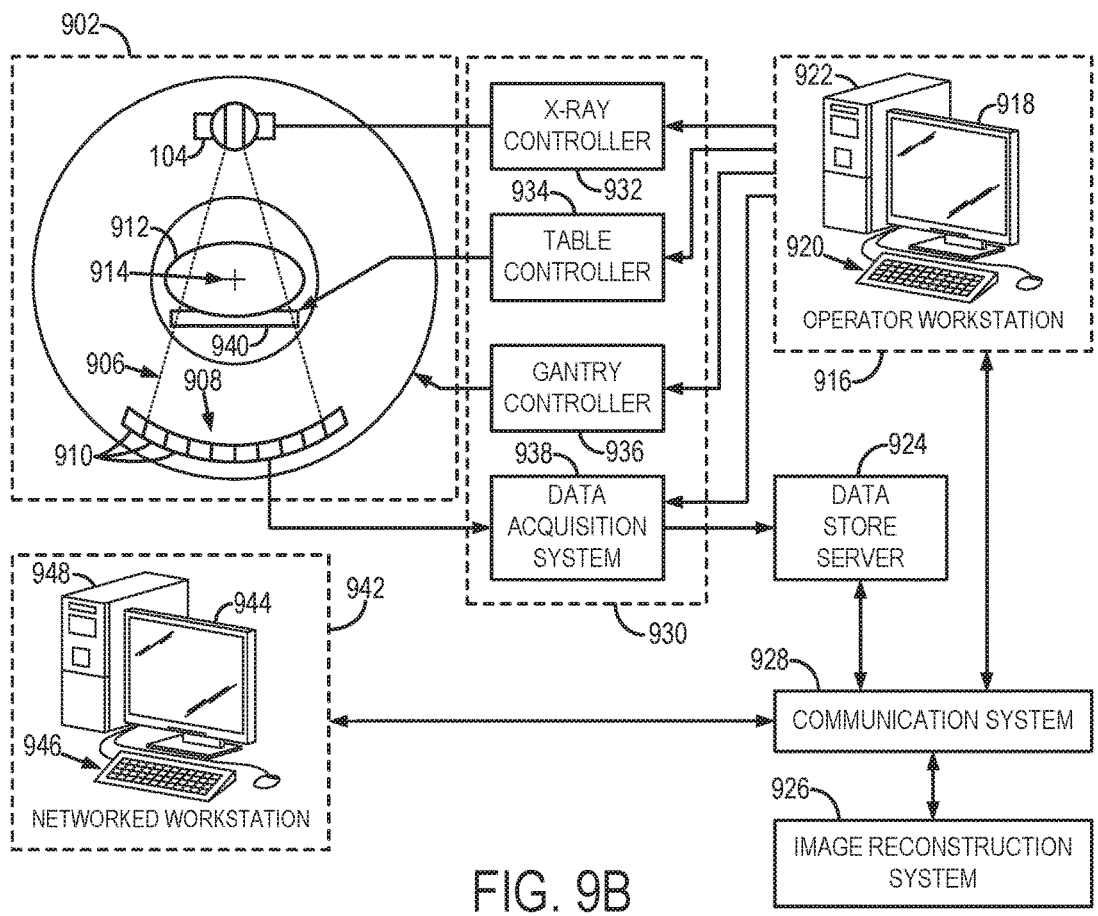
FIG. 9B is a schematic view of the CT system of FIG. 9A.

Referring to FIGS. 9A and 9B, a CT system 900 is illustrated that, as will be described, includes a rapid-rotation CT gantry 902 that includes at least one x-ray source 904 arranged to direct an x-ray beam 906, which may be a fan-beam or cone-beam of x-rays, toward a large-area detector array 908.

The detector array 908 includes a number of x-ray detector elements 910. As described, the detector array 908 may have a large area and, thus, a corresponding number of detector elements 910. For example, the large-area detector array may 908 achieve a data acquisition of 256-320 slices simultaneously. Together, the x-ray detector elements 910 sense the projected x-rays 906 that pass through a subject 912, such as a medical patient or an object undergoing examination, which is positioned in the CT system 900. Each x-ray detector element 910 produces an electrical signal that may represent the intensity of an impinging x-ray beam and, hence, the attenuation of the beam as it passes through the subject 912. In some configurations, each x-ray detector 910 is capable of counting the number of x-ray photons that impinge upon the detector 910. During a scan to acquire x-ray projection data, the gantry 902 and the components mounted thereon rotate about a center of rotation 914 located within the CT system 900.

The CT system 900 also includes an operator workstation 916, which typically includes a display 918; one or more input devices 920, such as a keyboard and mouse; and a computer processor 922. The computer processor 922 may include a commercially available programmable machine running a commercially available operating system. The operator workstation 916 provides the operator interface that enables scanning control parameters to be entered into the CT system 900. In general, the operator workstation 916 is in communication with a data store server 924 and an image reconstruction system 926. By way of example, the operator workstation 916, data store server 924, and image reconstruction system 926 may be connected via a communication system 928, which may include any suitable network connection, whether wired, wireless, or a combination of both. As an example, the communication system 928 may include both proprietary or dedicated networks, as well as open networks, such as the internet.

The operator workstation 916 is also in communication with a control system 930 that controls operation of the CT system 900. The control system 930 generally includes an x-ray controller 932, a table controller 934, a gantry controller 936, and a data acquisition system 938. The x-ray controller 932 provides power and timing signals to the x-ray source 904 and the gantry controller 936 controls the rotational speed and position of the gantry 902. The table controller 934 controls a table 940 to position the subject 912 in the gantry 902 of the CT system 900.

The DAS 938 samples data from the detector elements 910 and converts the data to digital signals for subsequent processing. For instance, digitized x-ray data is communicated from the DAS 938 to the data store server 924. The image reconstruction system 926 then retrieves the x-ray data from the data store server 924 and reconstructs an image therefrom. The image reconstruction system 926 may include a commercially available computer processor, or may be a highly parallel computer architecture, such as a system that includes multiple-core processors and massively parallel, high-density computing devices. Optionally, image reconstruction can also be performed on the processor 922 in the operator workstation 916. Reconstructed images can then be communicated back to the data store server 924 for storage or to the operator workstation 916 to be displayed to the operator or clinician.

The CT system 900 may also include one or more networked workstations 942. By way of example, a networked workstation 942 may include a display 944; one or more input devices 946, such as a keyboard and mouse; and a processor 948. The networked workstation 942 may be located within the same facility as the operator workstation 916, or in a different facility, such as a different healthcare institution or clinic. Data may be exchanged between components of the CT system 900 in any suitable format, such as in accordance with the transmission control protocol ("TCP"), the internet protocol ("IP"), or other known or suitable protocols.

The detector array 908 may have a large area and, thus, a corresponding number of detector elements 910. Again, the large-area detector array may 908 achieve a data acquisition of 256-320 slices simultaneously. Thus, utilizing the above-described CT system 900, full CT images can be generated at rates on the order of 3 per second. Each volume is acquired using about 300 projections. So, for a 0.3 second acquisition the projection duration is about 1 millisecond. Using this system 900, constraining volumes can be generated from each of the vascular volumes obtained during the sequential rotations of the gantry 902. Optionally, a constraining image can be generated from all the vascular volumes obtained over a 5-10 second series of rotations (up to about 30 volumes). When the shorter-term constraining images are used, the constraining image is sparser and leads to improved reconstruction from the projections used to form it.

As will be described, the above-described systems and methods allow the use of gantry-based, CT systems to provide quantitative velocity and flow measurements. That is, traditional CT-angiography using gantry-based such as illustrated in FIGS. 9A and 9B may be used to provide quantitative information and display velocity and flow information with each CTA acquisition. For example, quantitative flow and velocity measurements may be provided using gantry-based, CT systems in combination with additional techniques, such as will be described.

Figure 10:
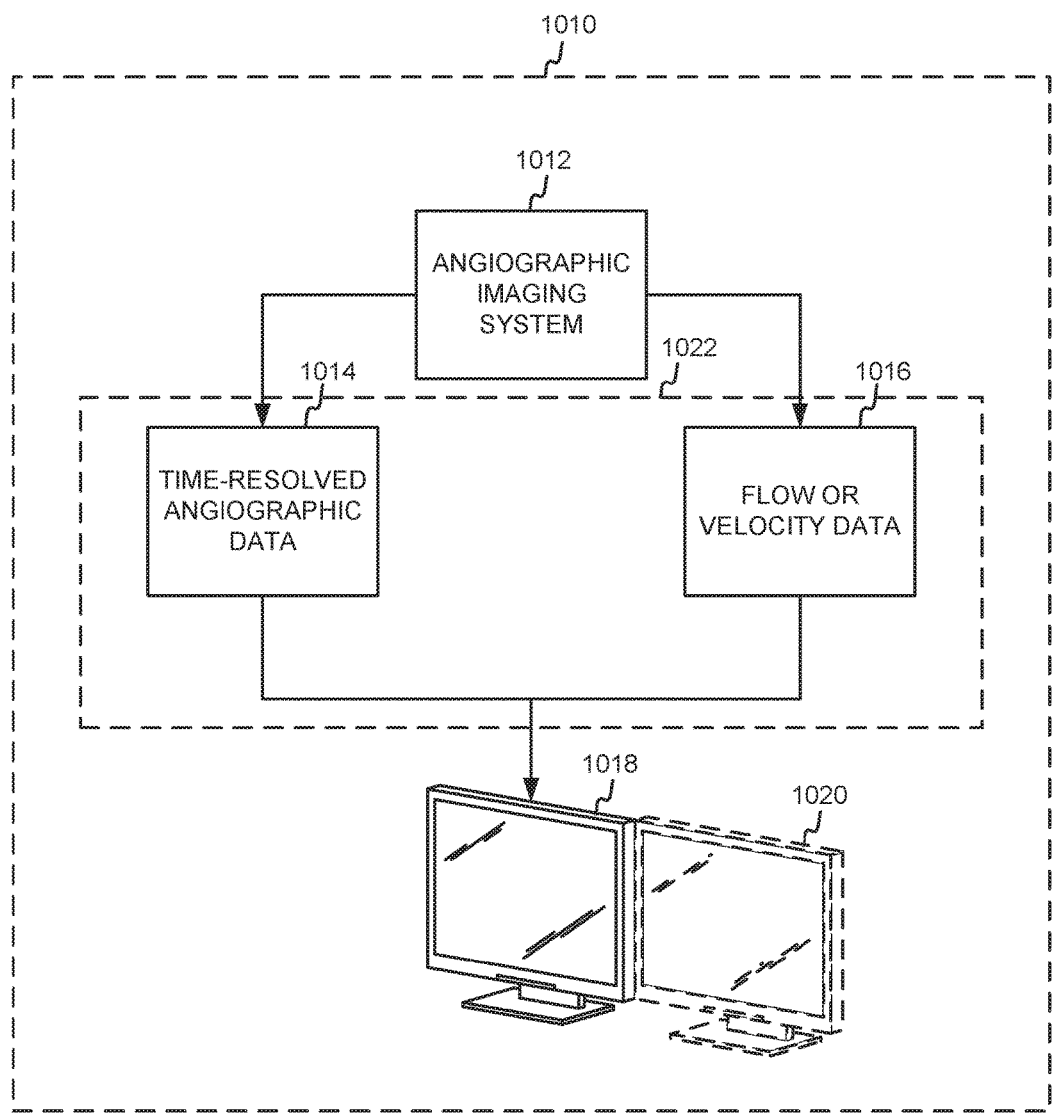
FIG. 10 is a schematic view of an angiographic processing and display system that may include the system of FIGS. 9A and 9B to provide quantitative CT angiography images.

Referring to FIG. 10, an overall system 1010 for creating time-resolved angiographic images having flow or velocity information using a traditional gantry-based CT system 900 is provided. In particular, the system 1010 includes an angiographic imaging system 1012. The angiographic imaging system 1012 is the gantry-based CT system 900 of FIG. 9, which can be conceptualized as delivering time-resolved angiographic data 1014 and flow or velocity data 1016. The time-resolved angiographic data 1014 and flow or velocity data 1016 can be processed and provided to a clinician via a display 1018. As will be further described, the information may be provided to the clinician using multiple displays including a first display 1018 and a secondary display 1020 or multiple additional displays. As will also be described, the process of deriving velocity or flow data can be performed partially or in whole using an image processing system, which may include a graphics processing unit (GPU) or other processor, including a central processing unit (CPU).

The above-described system 1010 can be used to acquire raw angiographic data that can then be processed to generate a time-resolved 3D angiographic image in the form of a 4D DSA image. The steps for a process of ultrafast quantitative CTA using a gantry-based CT system, such as illustrated in FIGS. 9A-10 will be described. When seeking to perform quantitative CTA using a gantry-based CT system, the above-described concepts for 4D DSA or HYPR may be applied. That is, as will be described, CTA images are generated using subtracted projections obtained by a mask scan with no contrast and a series of scans following IV iodine injection. Applying the above-described concepts for 4D DSA or HYPR to this process yields substantial clinical benefits. However, a variety of refinements and improvements are provided herein to make the process clinically applicable.

Figure 11A:
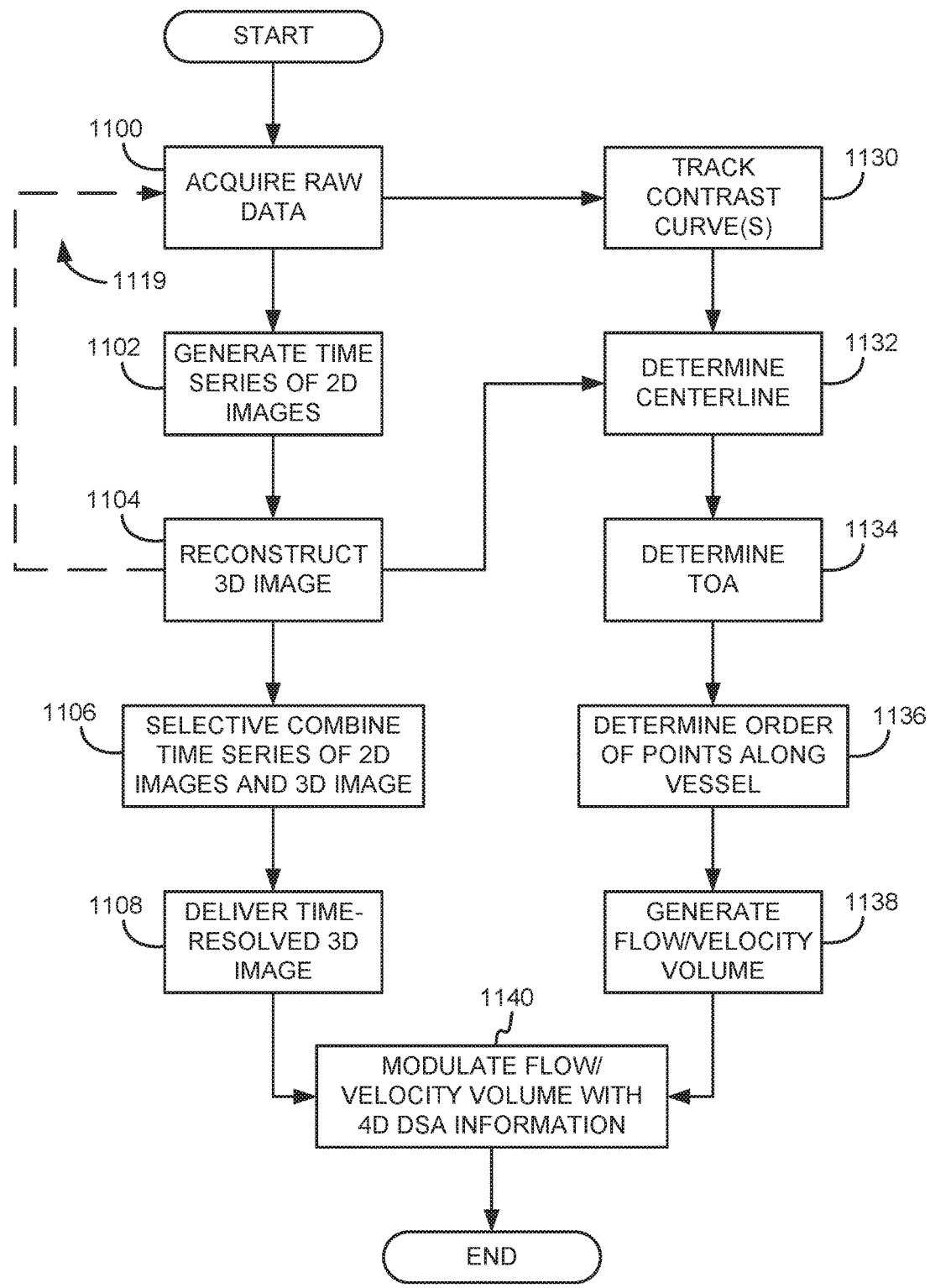
FIG. 11A is a flow chart setting forth some example steps for producing a 4D-DSA images with flow or velocity information using the system of FIG. 10.

Referring to FIG. 11A, a process for creating quantitative CTA images begins at process block 1100 with the acquisition of image data from a region-of-interest in a subject using the gantry-based CT system 900 of FIG. 9A. At process block 1102, a time-series of 2D images is generated from at least a portion of the acquired image data. The time-series of 2D images can have a high temporal and spatial resolution and may include images acquired at different angles around the subject. At process block 1104, a 3D image of the subject is reconstructed from the acquired image data. Individual projections used to reconstruct this 3D image may themselves convey some degree of temporal information; however, the reconstructed 3D image itself is substantially free of temporal resolution. For brevity, the 3D image substantially without temporal resolution and the time-series of 2D images may simply be referred to as the "3D image" and "2D images," respectively.

At process block 1106, the time-series of 2D images and the static 3D image are selectively combined so that the temporal information included in the 2D images is imparted into the 3D image. This results in the production of a time-resolved 3D image of the subject with high temporal and spatial resolution, which may be referred to as a 4D DSA image. This selective combination of the datasets generally involves the steps of (1) registering the 2D images to the 3D image, (2) projecting the attenuation value of the pixels in the 2D images into the 3D image, and (3) weighting the 3D image with the projected values for each individual frame of the time-series of 2D images. It is contemplated that the temporal weighting in step (3) may involve multiplying the projected pixel values with the 3D image. These three steps, which can be referred to as "multiplicative projection processing" (MPP), may be accompanied by additional steps to improve image quality or reduce the prevalence of errors and artifacts. For example, the intensity values of pixels and voxels in the 2D images and 3D image produced at process blocks 1102 and 1104 may quantify an x-ray attenuation level at a given location in the subject. These attenuation levels may not be preserved when multiplying the 3D image with projected pixel values. Accordingly, more accurate indications of the attenuation levels may be restored using the intensity value at each voxel in the time-resolved 3D image, for example, by taking the n-th root, if (n−1) different sets of 2D images are used, to weight the 3D image.

The 2D images and 3D image produced at process blocks 1102 and 1104, respectively, can be produced using DSA techniques. That is, 2D images depicting the subject's vasculature can be produced by reconstructing image data acquired as a bolus of contrast passes through the vasculature and subtracting out a pre-contrast, or "mask," image acquired before the administration of contrast agent. Likewise, a 3D image of the same vascular structures can be produced by reconstructing image data acquired as contrast agent occupies the vasculature and subtracting out a mask image to remove signal associated with non-vascular structures.

However, unlike the C-arm based implementations, the data acquired on gantry-based CT scanners generally uses intravenous (IV) rather than intra-arterial (IA) injections. Thus, a time-resolved 3D image produced by combining the DSA images is provided at process block 1108, which depicts the subject's vascular structures with both excellent spatial and excellent temporal resolution and may thus be referred to as a 4D-DSA image. As used herein, this time-resolved 3D image may also be referred to as a 4D image, a 4D angiographic image, or a 4D DSA image.

Figure 11B:
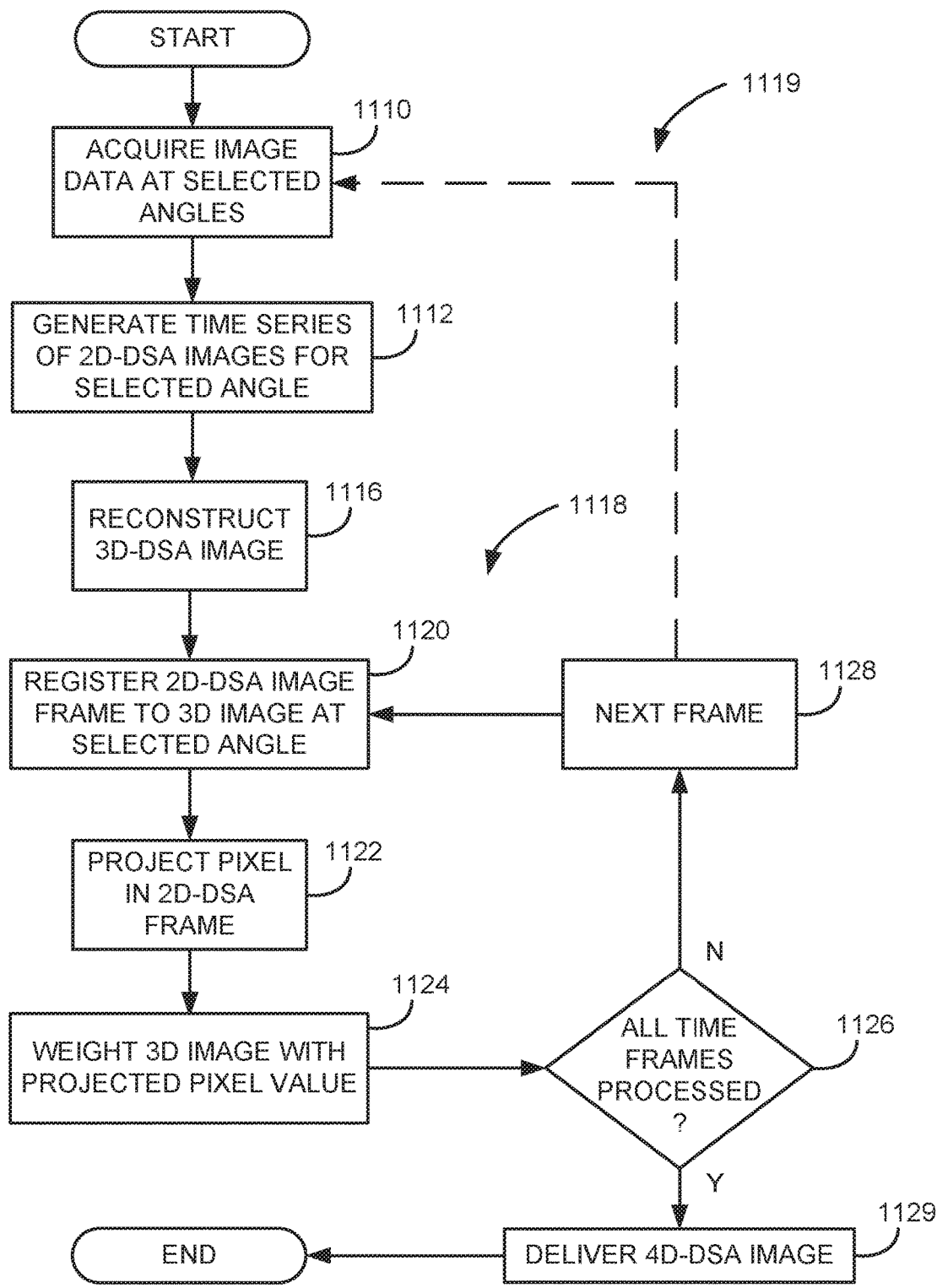
FIG. 11B is a flow chart providing further detail about the process of FIG. 11A.

Referring to FIG. 11B, a more specific implementation of the above-described process can be employed to produce a 4D-DSA image of a subject using a rotational, gantry-based x-ray system. In this case, the process begins at process block 1110, when time-resolved image data from a ROI in the subject is acquired using the gantry-based CT system 900 of FIG. 9A. Using the above-discussed DSA techniques, a time-series of 2D-DSA images at selected angles about the ROI is generated at process block 1112. These 2D-DSA images depict the contrast agent passing through and enhancing venous structures in the ROI. A 3D-DSA image is reconstructed at process block 1116 from the acquired image data.

Referring now to FIGS. 11A and 11B, the images produced thus far can be selectively combined with the steps indicated generally at 1118 to produce a 4D-DSA image 1108 with the detailed 3D resolution of the 3D-DSA image and the temporal resolution of the time-series of 2D-DSA images. Specifically, the reconstruction is accomplished by back-projecting the acquired projections through a conventional CTA volume that is acquired using a mask revolution and several iodine enhanced revolutions. At process block 1120, a frame of the 2D-DSA image is registered to the 3D-DSA image at the selected angle and, at process block 1122, the values of the pixels in the 2D-DSA frame are projected along a line passing through each respective pixel in a direction perpendicular to the plane of the 2D-DSA frame. At process block 1124, the 3D-DSA image is weighted by the values projected from the 2D-DSA frame to produce the 4D-DSA image. This may include multiplying the projected values with the voxels of the 3D image that they intersect.

At decision block 1126 of FIG. 11B, if all of the frames have yet to be processed, the process moves to the next frame of the time-series of 2D-DSA images at process block 1128 and repeats the selective combination process generally designated at 1118. This cycle continues until, at decision block 1126, it is determined that a 4D-DSA image has been generated for all relevant time frames. The 4D-DSA image can thus be delivered at process block 1129.

Importantly, as indicated at 1119, the above-described process need not wait until all data is acquired. Instead, the CTA images can advantageously be acquired at various stages throughout the contrast passage and, via loop 119, intermediate CTA images can be created to form an ongoing set of constraining images. In this way, one does not need to wait for a constraining image to be formed from the entire contrast passage. This is facilitated by the speed of the gantry-based CT system. That is, in the C-arm CTA applications, the formation of a 3D vascular volume can be compromised by the uneven signal associated with the inflow of contrast. This leads to inaccurate reconstruction of the 3D volume, but is necessary to get temporal information. The intermediate or progressive constraining images are sparser and provide fewer overlapping vessels. Vascular overlap is one factor that can limit temporal precision with C-arm CTA. Thus, controlling vascular overlap leads to more accurate time resolved vascular volumes.

That is, "overlap artifacts" or "shadow artifacts" created by overlapping vessels can be controlled by selecting intermediate constraining images, for example, formed by a few frames ahead of and a few frames behind the frame being reconstructed. As one example, the intermediate constraining images may be formed from a range of projections acquired over a period of 5 or greater seconds, or even 10 or more seconds. As another example, the constraining images may be formed at times corresponding to the CT frame rate. In this case, constraining images may be formed at a rate of 1 per second or a few per second. This process is more effective for controlling overlap artifacts than, for example, thresholding alone, which may not adequately control against overlap. Thus, ongoing projections are backprojected into the ongoing series of intermediate constraining images. Furthermore, since IV datasets are inherently less sparse than IA datasets, creating these intermediate constraining images helps to ensure that sparse images are used for the reconstruction.

Referring again to FIG. 11A, the above-described 4D DSA process can be augmented to track contrast curves at process block 1130. This information, as will be described, allows the above-described 4D DSA frames to be augmented so that the voxels reflect both iodine concentration and user selected temporal parameters, such as time of arrival, blood flow velocity, and flow. To do so, at process block 1132, the centerline of each vessel is determined. A vascular centerline can be determined from the constraining image and vascular branches are be defined based thereon. At each point along the centerline in each branch, an iodine signal curve can be determined, as will be described.

The centerline of the vessels can be found using a variety of techniques. As a non-limiting example, a process such as automated 4D flow whole vessel segmentation and quantification using centerline extraction. Skeletonization on a binary 3D DSA volume can be performed according to, as a non-limiting example, a thinning procedure suitable for elongated objects such as blood vessels, resulting in a one-voxel wide vessel centerline representation.

At process block 1134, a TOA curve is generated for each voxel. In one form, a threshold may be compared to the arrival time curve at any position in a vessel. However, such a process is subject to noise. Instead the TOA curve may be calculated by taking the first temporal moment of the contrast curve normalized by an integral over the contrast curve:

$$TOA(x) = \frac{\int C(t,x)t\,dt}{\int C(t,x)dt}; \quad (3)$$

where x is the vector 3D position along the centerline and C is time dependent and spatially dependent contrast curve. Thus, TOA is calculated by using the first moment of the frame time weighted by the contrast arrival curve and normalized by the integral of the contrast arrival curve. This process generates a temporal parameter with good SNR for each voxel reflecting the advancement of the bolus and does so using the statistical information from the entire contrast curve rather than the value at a specific time.

For each point x, the inverse of the slope of TOA vs. x, namely dx/dt provides a local estimate of the average blood speed over the cardiac cycle. Thus, local velocity is calculated as the inverse of the slope calculated. The gradient of the TOA versus position curve provides velocity.

Figure 12:
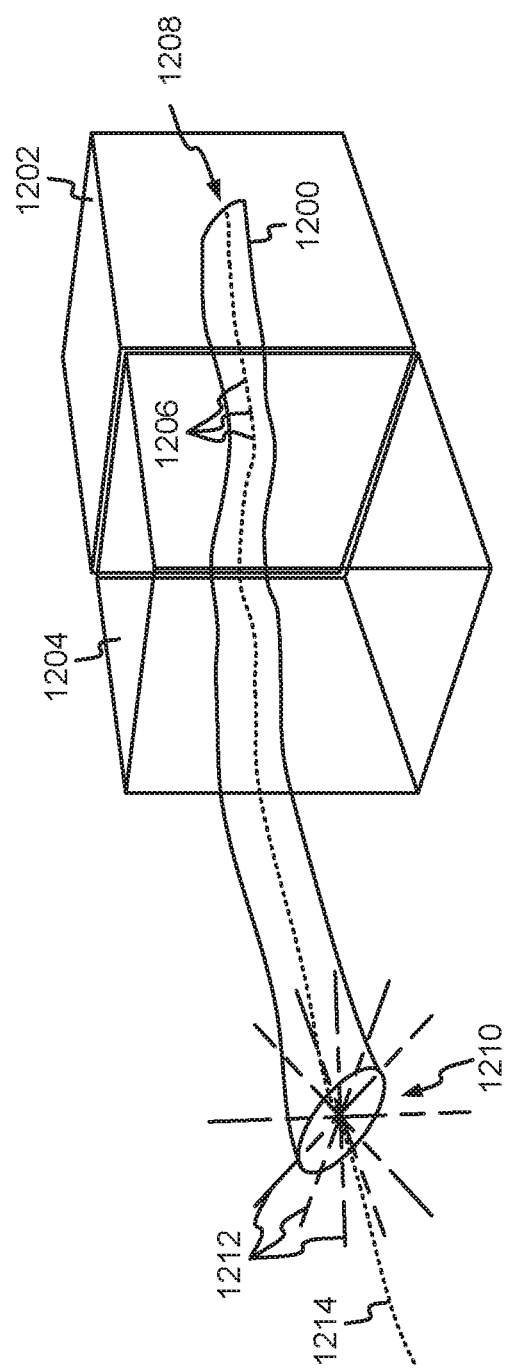
FIG. 12 is a schematic illustration of a volume analysis for flow or velocity information processing in accordance with the present disclosure.

At process block 1136, to fit the slope of the TOA values determined by Equation 3, the order of points along a given vessel in which velocity is to be measured may be determined. For example, referring to FIG. 12, a schematic illustration of a vessel 1200 is provided. To determine the order of points along the vessel 1200 at process block 1136 of FIG. 11A, a marching cubes algorithm may be used. In doing so, a series of marching cubes 1202, 1204 are used to find the order and position of points 1206 along a centerline 1208 of the vessel 1200. Vessel branch endpoints and junction points can be automatically identified and labeled within the vascular tree to produce a unique branch identification for each vessel.

Alternatively, a wider range of vessels and associated velocities may be processed automatically using a rotating mask process, which may rotate in 3D, such that the rate of change of TOA values along the centerline 1208 can be used to estimate velocity. Alternatively, the complete centerline data may be used to determine the local direction of the centerline 1208 in order to calculate the local TOA gradient of the TOA, such as described above, at each point 1206. This rotating mask algorithm uses rotating binary masks 1210 to determine the direction of the centerline 1210 by positioning a plurality of masks 1212 along a potential centerline 1214 and calculating a probability measure for each pixel that a given mask 1212 is aligned with the potential centerline 1214. The mask 1212 is rotated in 3D to find the orientation that has the highest correlation with the local centerline 1208. This process controls against the need to trace the centerline 1208 through bifurcations because the rotating mask 1212 can be used to automatically track centerlines through bifurcations. Thus, velocity can be calculated at each point 1206 in the vascular volume 1208 without having to proceed step by step through the vascular tree.

In the C-arm CTA applications, the formation of a 3D vascular volume can be compromised by the uneven signal associated with the inflow of contrast. This leads to inaccurate reconstruction of the 3D volume, but is necessary to get temporal information. With gantry-based CT scanners that can rotate 2-3 times per second, the inconsistencies in the projection signal used to form the intermediate CTA vascular volumes will be reduced leading to more accurate vessel cross-sections. As described above, an ingoing progression of intermediate constraining images may be used to provide more accurate cross-sectional areas and therefore more accurate centerline determination. This leads to more accurate velocity and flow estimations.

Regardless of the particular algorithm utilized, determining the centerline inside complex structures, such as arteriovenous malformations (AVMs) and aneurysms, can be difficult. Even if the centerline or centerlines of a particular complex structure cannot be adequately determined, the above-described systems and methods can be used to determine centerlines and velocities of the vessels entering and exiting these complex structure. When a region where the determination of the centerline may be unreliable, the above-described systems and methods can insert the grey scale 4D DSA information into the color display or otherwise indicate that the flow information is not available in that complex structure. Nevertheless, the clinician's needs are met by providing the flow information entering and exiting the complex structure.

Referring again to FIG. 11A, at process block 1138, the derived velocity and/or direction information can be used to generate a velocity volume. The velocity volume may be created using a color lookup table or other memory-storage mechanism. The lookup table or other mechanism may store velocity values or ranges and associated color codings. As such, the derived velocity information can be compared to the color lookup table or other memory-storage mechanism to generate flow/velocity volumes that are color coded. At process block 1140, the flow/velocity volume, and associated color information, is combined with the 4D DSA images. More particularly, at process block 140, the volume may be modulated by the 4D DSA intensity values at each point in time. For example, the volume may be subjected to a color preserving multiplication by each of the time resolved 4D DSA time frame volumes. As such, the color-coded voxel is also modulated by the voxel intensity to, thereby, reflect both time and iodine concentration.

Thus, the time resolved CTA volumes can be displayed in color where the color represents either average segmental velocity, flow (obtained by multiplying by an average area measurement obtained from the constraining image), or local segmental velocity (obtained by dividing the branch flow by the local area). Further information on determining velocity information and color coding based therein is provided in co-pending U.S. application Ser. No. 14/643,853, which is incorporated herein by reference in its entirety.

As will be described, the present disclosure provides a system and method that can deliver 4D DSA images including information about dynamic physiological characteristics of the structures that are spatially and temporally resolved in the 4D DSA images. That is, while 4D DSA images, by definition, are spatially resolved in three dimensions and also temporally resolved, the present disclosure provides systems and methods to provide further information to a clinician that can be coupled with the 4D DSA images, for example, to communicate flow or velocity information within the 4D DSA images. Furthermore, the present disclosure can derive information about the dynamic physiological characteristics, such as flow direction or velocity, from the 4D DSA data. For example, as will be described, the systems and methods of the present disclosure can derive pulsatile waveforms, such as generated by the pulsatile flow of blood through vessels or artificially created by dynamic injections, from the subject being studied and use the pulsatile waveforms, as well as the time-resolved three dimensional information regarding the vessel to derive dynamic physiological information, such as flow direction or velocity, without relying on TOA information.

Traditional DSA or non-time-resolved, three-dimensional (3D) imaging techniques can fail when attempting to determine a distance, such as $\Delta x$, or time shift, such as $\Delta t$, relative to a given vessel. If the imaging data or the technique used to acquire the data lacks temporal information, it is not possible to determine a time shift, $\Delta t$. Furthermore, even if temporal information is available, such as when using traditional DSA, it can be difficult to accurately determine a distance, $\Delta x$, using a maximum intensity projection (MIP). That is, a MIP or other, non-4D image, may not allow one to correctly estimate the length of path along a given vessel, such as when the vessel extends along a circuitous path within the plane of the projection. However, using the systems and methods of the present disclosure, it is possible to correctly estimate the path length along the vessels and, using systems and methods that will be described, using a selected distance along a given vessel to determine phase shifts that can be correlated with flow direction or velocity within the vessel.

As will be described, the systems and methods of the present disclosure can consider two different points along a vessel separated by a distance, $\Delta x$ and determine a pulsatile waveform that is delayed in time by an amount $\Delta t$ across the distance, $\Delta x$. The systems and methods of the present disclosure can use the time shift to then determine the flow direction and/or velocity using $\Delta x$ and $\Delta t$. This information can be coupled with the 4D DSA images to provide a clinician with valuable dynamic, physiological information.

Figure 13:
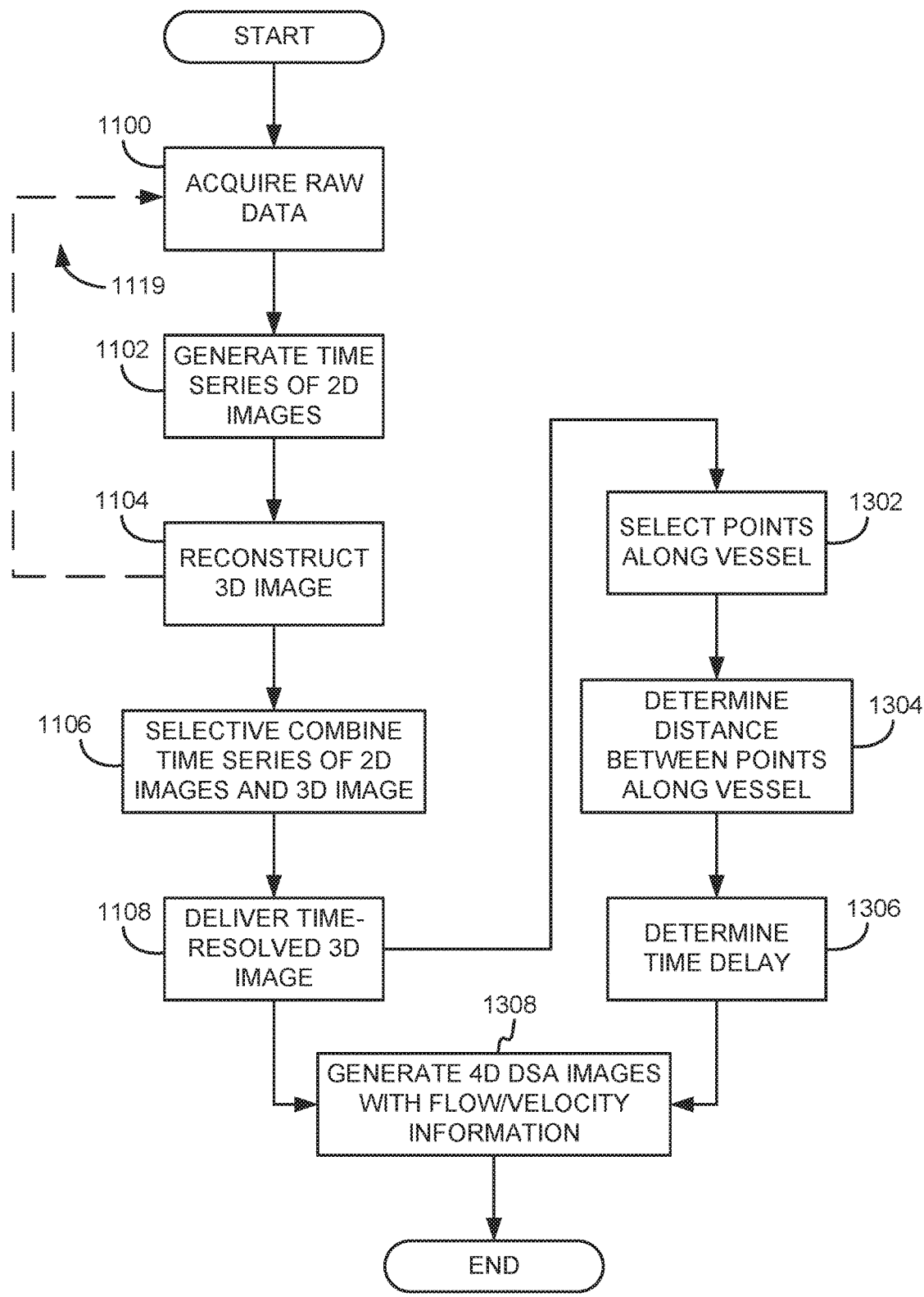
FIG. 13 is a flow chart setting forth some example steps of another process for producing 4D-DSA images with flow or velocity information.
Figure 14:
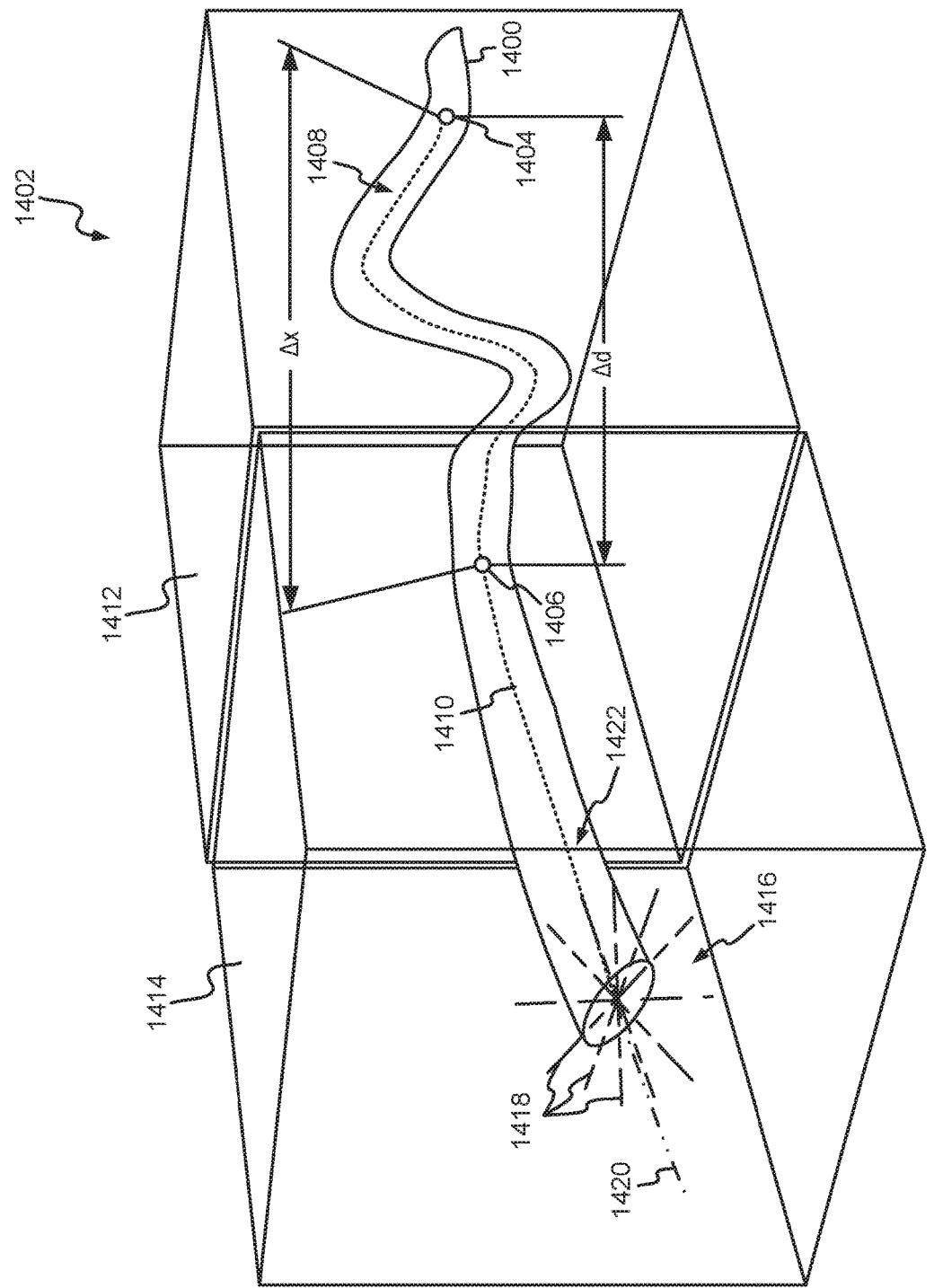
FIG. 14 is a schematic illustration of another volume analysis for flow or velocity information processing in accordance with the present disclosure.

Specifically, referring to FIG. 13, a 4D DSA process is provided that includes steps 1100-1108, such as described above with respect to FIG. 11A. Thereafter, at process block 1302, points are selected that are displaced from one another along a vessel in the 4D DSA images. At process block 1304, the distance between the selected points along the vessel can be determined. For example, referring to FIG. 14, a vessel 1400 is illustrated that extends along a circuitous route through a three dimensional space 1402, which can be resolved in three dimensions and time via a 4D DSA image created as described above. Using the information available in a 4D DSA dataset, two points 1404, 1406 can be selected that are separated along the vessel 1400 by a distance, Δx, along a path 1408 through the vessel 1400, which as will be described, may follow a centerline 1410 of the vessel. Despite the path 1408 being curved and, thus, having a distance, Δx, that is greater than an absolute distance, Δd, separating the two points 1404, 1406, the use of 4D DSA data allows the distance, Δx, along a path 1408 through the vessel 1400 to be determined.

As one non-limiting example, a marching cubes algorithm may be used to determine a centerline 1410 of the vessel 1400. In doing so, a series of marching cubes 1412, 1414 may be used to find the order and position of points along the centerline 1410 of the vessel 1400. Alternatively, a wider range of vessels and associated velocities may be processed automatically using a rotating mask process, which may rotate in 3D. This rotating mask algorithm uses rotating binary masks 1416 to determine the direction of the centerline 1410 by positioning a plurality of masks 1418 along a potential centerline 1420 and calculating a probability measure for each pixel that a given mask 1418 is aligned with the potential centerline 1420. The mask 1418 is rotated in 3D to find the orientation that has the highest correlation with the local centerline 1422.

Referring again to FIG. 13, with distance, Δx, between the points along the vessel determined, a variety of parameters may be calculated. For example, the time-resolved, 3D image data (4D DSA data) can be used to determine a diameter of the vessel. Also, the 4D DSA data can be used to determine a time delay, Δt, at process block 1306. Determining the time delay, Δt, at process block 1306 may be achieved using a variety of methods. For example, pulsatility through the vessel may be used as a mechanism to discern time delays that can then be included in 4D DSA images with flow or velocity information that are generated/displayed at process block 1308. Further information on using pulsatility to determine flow or velocity information is provided in co-pending U.S. application Ser. No. 14/855,209, which is incorporated herein by reference in its entirety.

For example, once the two 1404, 1406 are selected, respective time attenuation curves with pulsatile flow can be derived from the 4D DSA data. A check of the similarity of the curves using, for example, cross correlation versus integer time frame shift can be performed to determine a cross correlation, despite noise. The minimum in the comparison curve versus the temporal shift value gives the Δt value that, when combined with Δx, provides the velocity of flow between the two selected points.

The above-described correlation/shift method can also be applied to determine the optimal spatial shift required to line up the signal versus distance curves at two points in time. That is, one can choose two time points and look at the spatial distribution at these two points in time and then determine the spatial shift required to line up the two spatial distributions using cross correlation, sum of squares, or other analysis. This method also provides a Δx and Δt from which velocity or flow can be calculated.

Again, the 4D DSA images may be encoded with flow/velocity information included. For example, the 4D DSA images may be color coded or animated to provide a spatially- and time-resolved report to a clinician that also includes information about the underlying dynamic physiological performance, such as through flow direction or velocity.

Figure 15A:
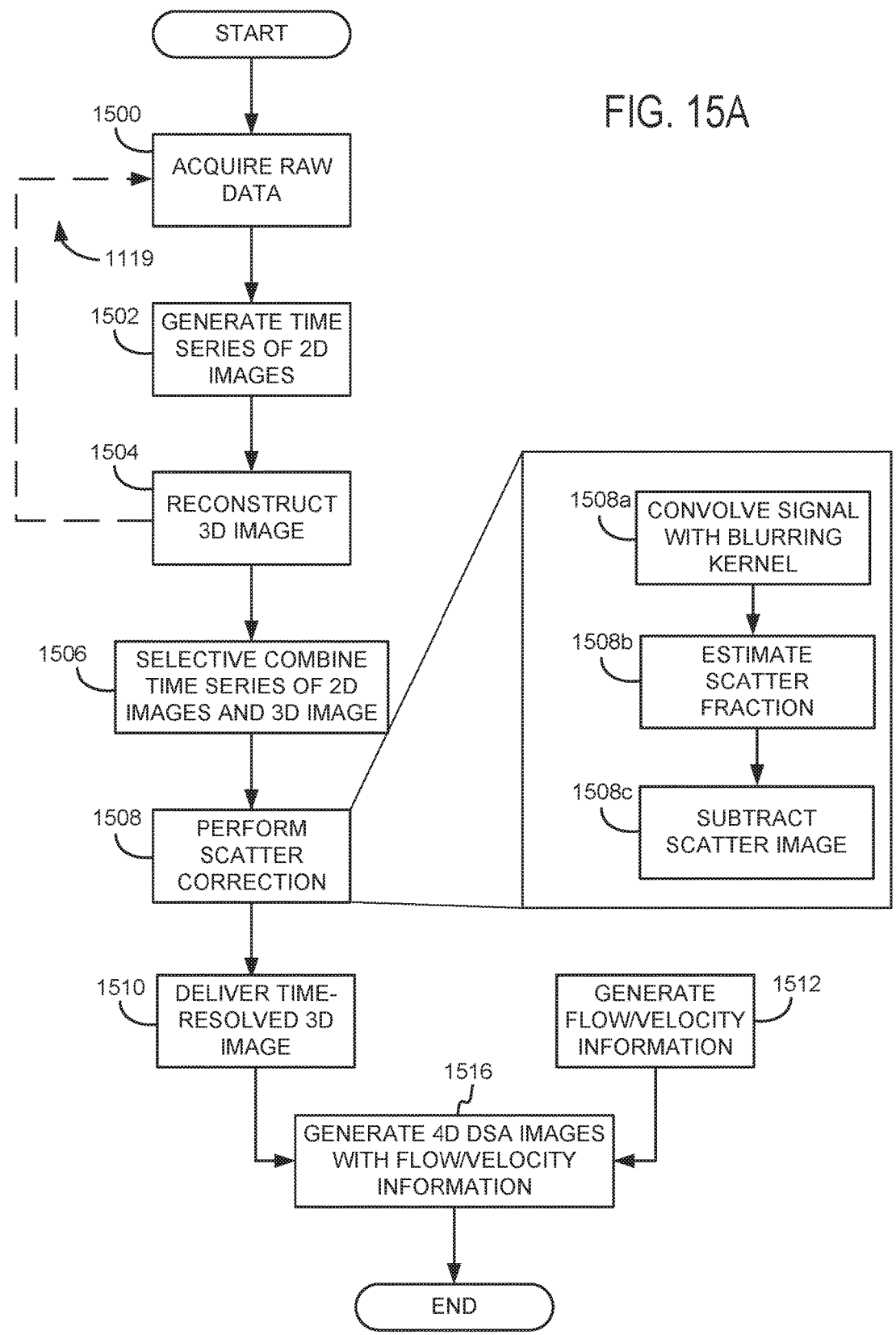
FIG. 15A is a flow chart setting forth a process for ultrafast quantitative CT angiography using a gantry-based CT system in accordance with the present disclosure.
Figure 15B:
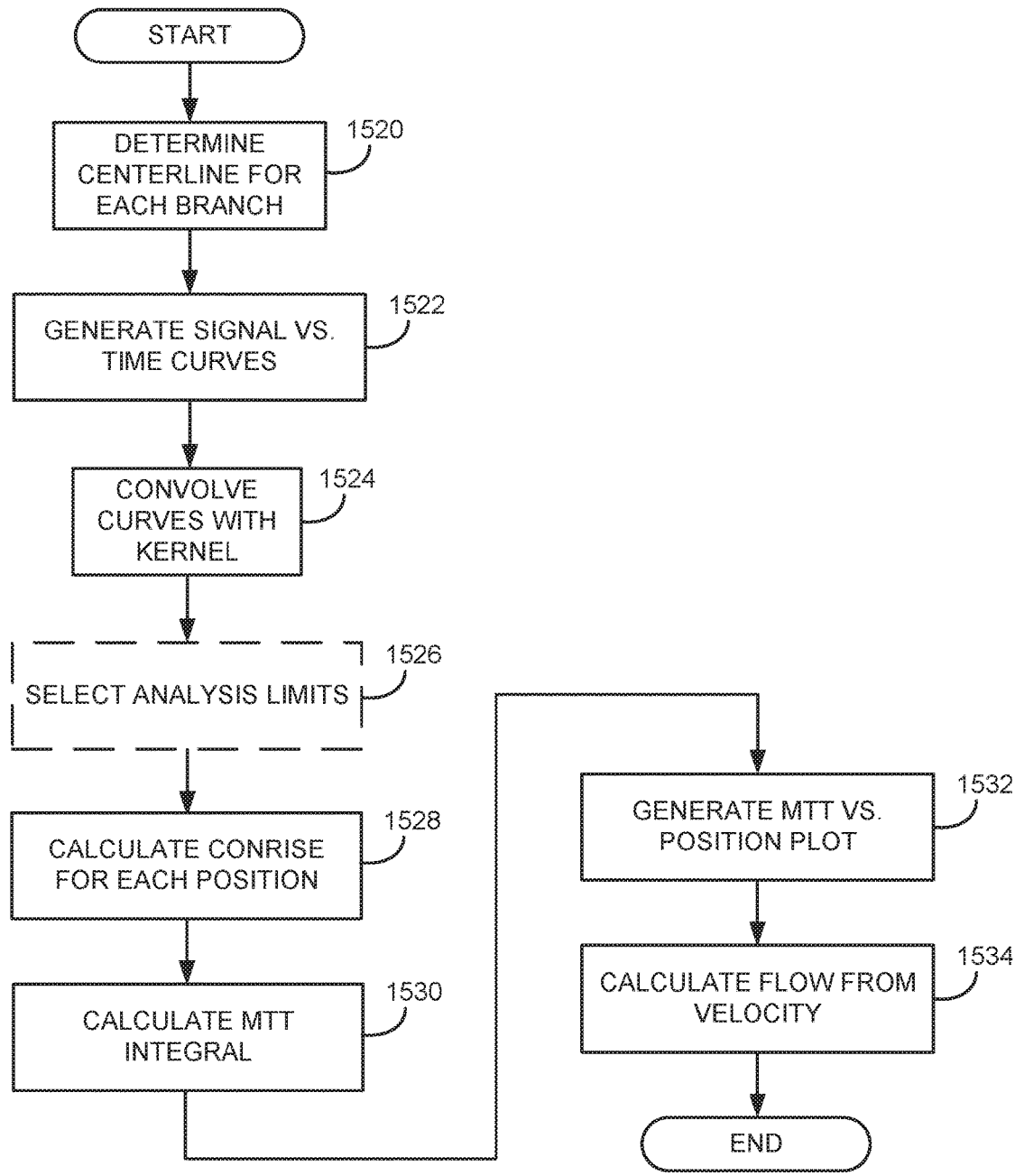
FIG. 15B is a flow chart setting forth a process for determining flow and/or velocity using a gantry-based CT system in accordance with the present disclosure.

Referring to FIGS. 15A and 15B, the above-described processes may be further adapted to address additional constraints presented by the use of the gantry-based CT system 900 of FIG. 9A to create quantitative CTA images. As with the above-described processes, at process block 1500 image data is acquired from a region-of-interest in a subject using the gantry-based CT system 900 of FIG. 9A. At process block 1502, a time-series of 2D images is generated from at least a portion of the acquired image data. The time-series of 2D images can have a high temporal and spatial resolution and may include images acquired at different angles around the subject. At process block 1504, a 3D image of the subject is reconstructed from the acquired image data. Again, the reconstructed 3D image itself is substantially free of temporal resolution. For brevity, the 3D image substantially without temporal resolution and the time-series of 2D images may simply be referred to as the "3D image" and "2D images," respectively.

At process block 1506, the time-series of 2D images and the static 3D image are selectively combined so that the temporal information included in the 2D images is imparted into the 3D image. The 2D images and 3D image produced at process blocks 1502 and 1504, respectively, can be produced using DSA- or HYPR-based techniques. That is, 2D images depicting the subject's vasculature can be produced by reconstructing image data acquired as a bolus of contrast passes through the vasculature and subtracting out a pre-contrast, or "mask," image acquired before the administration of contrast agent. Likewise, a 3D image of the same vascular structures can be produced by reconstructing image data acquired as contrast agent occupies the vasculature and subtracting out a mask image to remove signal associated with non-vascular structures.

When scatter is not present, a mask M (without iodine) and fill projection F (with iodine) can be logarithmically subtracted to isolate the iodine signal. In traditional C-arm systems, scatter is generally negligible compared to the overall signal. However, when using a gantry-based CT system, scatter can present a substantial impediment to accurate subtraction. As such, as process block 1508, scatter correction may be performed.

Specifically, the mask M may be modeled as:

$$M = Ie^{(-ut^*t)} \quad (4);$$

where ut is the linear attenuation coefficient of tissue and t is the local tissue thickness in the projection direction. In this case, the fill projection may be modeled as:

$$F = Ie^{(-us^*t - ui^*ti)} \quad (5);$$

where ui is the iodine coefficient and ti is the iodine thickness. With these models in place, log(M/I)−log(F/I) gives ui*ti with no residual non-iodine signal.

Thus, if scatter is present a scatter term, S, can be added to equations 4 and 5 as:

$$M = Ie^{(-ut^*t)} + S \quad (4a);$$

$$F = Ie^{(-us^*t - ui^*ti)} + S \quad (5a).$$

Following therefrom:

$$\log M/I = \log(e^{(-ut^*t)} + S) \quad (6a);$$

$$\log F/I = \log(e^{(-us^*t - ui^*ti)} + S) \quad (6b);$$

which produces:

$$\log(M/I) - \log(F/I) = \frac{\log(e^{(-ut*t)} + S)}{\log(e^{-ut*t-ui*ti} + S)}; \quad (7)$$

which does not isolate the iodine signal, I, but shows uncancelled anatomic information modulating the iodine signal. When time-dependent iodine signal curves are used for estimating velocity, scattering thereby presents a substantial burden, because the anatomical variations will be time dependent as various projection angles are used and will corrupt the time variations of the iodine signal which are of interest. Accordingly, it is important to control against the scatter signal before performing the logarithmic subtraction.

When intra-arterial injections are used, the iodine signal is large and some corruption by the scatter can be tolerated. However, when intravenous iodine injections are used, the iodine signal is small and scatter can be comparable or greater than the primary intensity. Thus, scatter can present a substantial challenge when attempting to implement the above-described systems and methods on gantry-based systems, where the contrast is introduced intravenously. That is, in CTA performed using gantry-based systems such as described above, the injections are almost always intravenous injections. With older conventional CT systems with limited axial coverage, the scatter fraction relative to the primary radiation is smaller than in typical flat panel C-arm CT systems. However, in the some newer systems, the axial coverage is comparable to the flat panel systems and scatter creates substantial considerations.

As described above, the present disclosure provides for scatter control or scatter removal. For example, at process block 1508 of FIG. 15A, an estimate of the spatial distribution of scatter is obtained by convolving the detected primary signal (M or I) plus scatter with a large blurring kernel at process block 1508a. This strategy recognizes the scatter is a very low spatial frequency phenomenon. Thus, at each point in the detected projection image, the scatter fraction is estimated at process block 1508b and used to predict how much of the scatter image should be subtracted from the detected projection at process block 1508c. The scatter fraction is spatially dependent and will be larger in regions of low intensity where the primary radiation is small.

To assist with this process, lead blocker exposures can be done on a patient-equivalent phantom. The detected signal intensity behind the lead blockers provides a measure of the local scatter fraction and reveals how much of the blurred (scatter) image should be subtracted before doing the logarithmic subtraction. A look-up table of scatter fraction vs detected intensity, I, is generated to guide the scatter subtraction. This information can provide improved cancellation of anatomical signals and a more accurate estimate of the iodine temporal signal variations.

The above-described scatter control or removal process is but one strategy that can be used to address the challenges presented by scatter when attempting to implement the systems and methods of the present disclosure in a gantry-based CT system. That is, one example of a scatter estimation method that may be used is the Naimuddin algorithm, as described in Naimuddin S., Hasegawa B. H., Mistretta C. A. Scatter-glare correction using a convolution algorithm with variable weighting. Med Phys 14(3):330-334, 1987, which is incorporated herein by reference in its entirety.

After performing scatter correction, a time-resolved 3D image produced by combining the DSA images is provided at process block 1510, which depicts the subject's vascular structures with both excellent spatial and excellent temporal resolution and may thus be referred to as a 4D-DSA image. As described above, the 4D-DSA image data may be combined with flow/velocity information provided at process block 1512 to generate 4D-DSA images with flow/velocity information at process block 1516.

More particularly, referring to FIG. 15B, a process for generating the flow/velocity information provided at process block 1512 is illustrated. For example, as described above with respect to FIGS. 11A-14, a variety of processes may be used to derive and provide flow and/or velocity information to be illustrated in combination with the 4D-DSA images.

In one non-limiting example of a process for deriving such flow and/or velocity information, signal pulsatility may be used as described above. However, when attempting to discern flow and/or velocity information when utilizing gantry-based systems, the decreased pulsatility in the IV signal can make the above-described techniques relying on pulsatility for deriving flow or velocity information challenging. As such, as will be described, a mean transit time (MTT) method may be used to adjust for such confounding aspects. That is, the techniques described herein utilizing MTT can overcome the challenges of IV quantitative, gantry-based CTA with discerning flow or velocity because they does not rely on signal pulsatility.

Referring to FIG. 15B, to utilize MTT to derive flow or velocity information, the process begins by at process block 1520 with determining a centerline for each branch in a set of image, as described above. At process block 1522, signal vs. time curves are generated for a plurality of points along the centerline of each branch.

Then, at process block 1524, the signal vs. time curves may be convolved with a temporal kernel to reduce and/or remove effects of pulsatility. For example, the kernel may be formed of 10 or more frames, 20 or more frames, or 30 or more frames, including 20-30 frames. Optionally, at process block 1526, analysis limits may be selected. For example, the analysis may be limited to positions with integrated signal curves within a predetermined percentage of an average integral over all positions. Doing so can be used to control overlap and anomalous signals.

At process block 1528, a rising integrated signal (conrise) for each position is calculated using $t_{start}$ and $t_{end}$ where $t_{start}$ is typically where the curves start to rise and $t_{end}$ is before the curves all flatten out. In one non-limiting example, $t_{start}$ may be set to frame 40 and $t_{end}$ may be frame 120. At process block 1530, an MTT integral is calculated between a lower threshold fraction of $t_{end}$ and upper threshold fraction of $t_{end}$, for example, according to:

$$MTT = \int \frac{\text{signal}(t) * t}{\text{signal}(t)}. \quad (8)$$

This can be done for all chosen positions on the centerline and, at process block 1532, an MTT vs position plot can be generated. In this plot, MTT values can be set to zero for positions that have been excluded because of a down-vessel view criterion or the similarity criterion.

More particularly, to define the temporal interval over which the MTT may be calculated, the integration may start at a selected percent of the conrise for each position, such as, for example, 10%. The integration may then stop when a higher threshold is reached, such as a non-limiting example of 40%. Thus, MTT is calculated using Equation 8 and the process may be repeated over a wide range of high thresholds and $t_{ends}$.

Specifically, at process block 1534, this MTT curve is fit and the velocity is calculated from the inverse of the slope of the fit. Optionally, as a further refinement, the calculation of velocity can be done for a range of upper-time values called $t_{endlow}$ that are lower than the original $t_{end}$. Velocities can also be calculated for variations in the upper threshold fraction of the current $t_{endlow}$. These velocity estimates can be plotted, for example, on a meshplot, where a successful choice of parameters leads to a broad plateau of similar estimates for the velocity. The velocities calculated for these variations in parameters can be used to generate a histogram and the overall velocity estimate can be taken to be the position of the peak of this histogram.

Thus, the estimated velocity can be taken as the position of the peak velocity bin in the histogram or the average of all the velocity estimates. A mesh plot provides some perception of the rate at which the estimates change with the choices for the high conrise threshold and the $t_{ends}$.

As addressed above, it can be valuable to control against vessel overlap. Also, it can be valuable to control for errors injected by so-called "down-vessel" views. When 2D plot of signal vs position and time is created from an image frame that includes a view down a vessel extending away from the view, an obscuring band can be the result on the 2D plot, which corresponds to positions having down-vessel views. Inclusion of the down-vessel positions in the velocity estimates can lead to elevated velocity estimates. Thus, to compensate for such confounding factors, the above-described process can exclude any banded areas or entire views with banding caused by down-vessel views from velocity calculations. For example, such regions or views can be excluded based on the derivatives of the centerline. This can be done automatically to allow for the use of non-contiguous positions.

The above-described processes may be combined with other techniques, such as "spiral" or "helical" CT imaging, which allows continuous data collection while a subject is advanced through the CT gantry. Specifically, an x-ray source and detector are revolved around the subject as views are acquired at successive view angles and the subject is slowly moved axially through the gantry. This provides an uninterrupted volume of x-ray attenuation data. From this data, multiple contiguous or overlapping slices of arbitrary thickness can be reconstructed or a 3D image of a volume can be reconstructed. With spiral/helical CT angiography (CTA), vascular structures can be selectively visualized by choosing an appropriate delay after IV or IA injection of a contrast material. This gives excellent visualization of vessel lumina, stenoses, and lesions. The acquired data can then be displayed as described above.

However, by advancing the imaging plane at each successive projection time, the magnification of the projection image at the detector changes. Thus, the present disclosure contemplates that the above-described backprojection process can be adjusted such that the magnification is changed for each successive projection. To do so, the pitch of the scan can be determined and used to describes how fast the table is moved and, thereby, the change in magnification. Alternatively, a block matching can be performed to achieve a linear interpolation to identify the change in magnification. Further still, a calculated speed provided by the controller moving the table may be used to extrapolate the magnification. In any case, a magnification correction can be inserted into the above-described process.

The present invention has been described in terms of the preferred embodiment, and it should be appreciated that many equivalents, alternatives, variations, and modifications, aside from those expressly stated, are possible and within the scope of the invention. Therefore, the invention should not be limited to a particular described embodiment.

The invention claimed is:

1. A method for generating quantitative computed tomography (CT) angiographic images, the method comprising:
   acquiring a set of projection views forming CT angiographic image data of a patient using a projection duration of less than 50 milliseconds;
   producing a composite image from the CT angiographic image data that indicates an attenuation value at each composite image pixel of the patient;
   backprojecting each projection view in the CT angiographic image data and weighting a value backprojected into at image pixel by an attenuation value of a corresponding pixel in the composite image;
   summing backprojected values for each image pixel to produce a CT image of the patient;
   performing a scatter correction on at least one of the CT angiographic image data and the CT image of the patient;
   determining at least one of a flow direction or a velocity of flow with a vessel in the patient; and
   displaying the at least one of the flow direction or the velocity of flow with the vessel in the patient with the CT image of the patient to provide the quantitative CT angiographic images.

2. The method of claim 1 further comprising generating a time-series of two-dimensional images from at least a portion of the CT angiographic image data, reconstructing a three-dimensional image substantially without temporal resolution from at least a portion of CT angiographic image data, and producing a time-resolved three-dimensional image of the subject by selectively combining the three-dimensional image substantially without temporal resolution and the time-series of two-dimensional images.

3. The method of claim 2 further comprising determining a temporal parameter for each voxel of the time-resolved three-dimensional image to determine the at least one of the flow direction or the velocity of flow.

4. The method of claim 3 wherein the temporal parameter is a mean transit time (MTT) through the vessel in the patient.

5. The method of claim 2 further comprising superimposing a color coded display of the temporal parameter on at least one of the time-resolved three-dimensional image and a blood volume image generated from the three-dimensional image substantially without temporal resolution to display the at least one of the flow direction or the velocity of flow with the vessel in the patient with the CT image of the patient.

6. The method of claim 1 further comprising calculating a mean transit time (MTT) through the vessel in the patient to determine at least one of a flow direction or a velocity of flow with a vessel in the patient.

7. The method of claim 1 further comprising calculating a mean transit time (MTT) through the vessel in the patient to over an interval for each of a plurality of positions along the vessel to determine at least one of a flow direction or a velocity of flow with a vessel in the patient and wherein the MTT is calculated using a rising integrated signal (conrise) for the plurality of positions along the vessel in the patient.

8. The method of claim 1 further comprising deriving information about a movement of the patient during acquisition of the set of projection views forming CT angiographic image data and adjusting a magnification of each projection relative to the detector based on the information about the movement of the patient.

9. The method of claim 1 further comprising producing a series of intermediate composite images that progress along with the additional projection views forming CT angiographic image data.

10. A method for generating quantitative computed tomography (CT) angiographic images, the method comprising:
  acquiring a set of projection views forming CT angiographic image data of a patient using a projection duration of less than 50 milliseconds;
  producing a composite image from the CT angiographic image data that indicates an attenuation value at each composite image pixel of the patient;
  backprojecting each projection view in the CT angiographic image data and weighting a value backprojected into at image pixel by ban attenuation value of a corresponding pixel in the composite image;
  summing backprojected values for each image to produce a CT image of the patient;
  performing a scatter correction on at least one of the CT angiographic image data and the CT image of the patient;
  determining at least one of a flow direction or a velocity of flow with a vessel in the patient;
  displaying the at least one of the flow direction or the velocity of flow with the vessel in the patient with the CT image of the patient to provide the quantitative CT angiographic images; and
  further comprising, to preform the scatter correction:
    convolving the CT image of the patient with a blurring kernel to create a scatter image;
    at a plurality of points in the CT image of the patient, estimating a scatter fraction; and
    subtracting the scatter image from the CT image of the patient using the scatter fraction.

11. The method of claim 10 wherein the scatter image is spatially dependent to have larger values in regions of low signal intensity in the CT angiographic image data.

12. The method of claim 10 further comprising using lead blocker data or a look-up table of scatter fraction vs. detected intensity to estimate the scatter fraction.

13. A method for generating quantitative computed tomography (CT) angiographic images, the method comprising:
  acquiring a set of projection views forming CT angiographic image data of a patient using a projection duration of less than 50 milliseconds;
  producing a composite image from the CT angiographic image data that indicates an attenuation value at each composite image pixel of the patient;
  backprojecting each projection view in the CT angiographic image data and weighting a value backprojected into at image pixel by an attenuation value of a corresponding pixel in the composite image;
  summing backprojected values for each image pixel to produce a CT image of the patient;
  performing a scatter correction on at least one of the CT angiographic image data and the CT image of the patient;
  determining at least one of a flow direction or a velocity of flow with a vessel in the patient;
  displaying the at least one of the flow direction or the velocity of flow with the vessel in the patient with the CT image of the patient to provide the quantitative CT angiographic images; and
  further comprising:
    determining a centerline for the vessel in the patient using the CT image of the patient;
    generating signal vs. time curves for a plurality of points along the centerline of the vessel;
    convolving the signal vs. time curves with a temporal kernel to reduce effects of pulsatility;
    calculating a rising integrated signal (conrise) for a plurality of positions along the vessel in the patient; and
    calculating the MTT through the vessel in the patient over an interval selected based on the conrise for each of the plurality of positions.

14. The method of claim 13 further comprising generating the temporal kernel using a plurality of image frames from the CT angiographic image data.

15. The method of claim 13 further comprising generating a MTT curve based on the MTT through the vessel across the plurality of positions and deriving velocity using a slope of the MTT curve.

16. A system for generating quantitative computed tomography (CT) angiographic images, the system comprising:
  a rotatable gantry including a radiation source and a detector coupled thereto, wherein the rotatable gantry is configured to receive a patient to rotate the radiation source and the detector around the patient to acquire a set of projection views forming CT angiographic image data of the patient using a projection duration of less than 50 milliseconds;
  a computer system programmed to receive the CT angiographic image data from the detector and generate quantitative CT angiographic images by:
    producing a composite image that indicates an attenuation value at each composite image pixel of the patient;
    reconstructing the quantitative CT angiographic images of the patient by:
      backprojecting each projection view in the CT angiographic image data and weighting a value backprojected into at image pixel by an attenuation value of a corresponding pixel in the composite image;
      summing backprojected values for each image pixel to produce a CT image of the patient;
      performing a scatter correction on at least one of the CT angiographic image data and the CT image of the patient;
      determining at least one of a flow direction or a velocity of flow with a vessel in the patient; and
      combining the at least one of the flow direction or the velocity of flow with the vessel in the patient with the CT image of the patient to generate the quantitative CT angiographic images.

17. The system of claim 16 wherein the computer system is further programmed to generate quantitative CT angiographic images by generating a time-series of two-dimensional images from at least a portion of the CT angiographic image data, reconstruct a three-dimensional image substantially without temporal resolution from at least a portion of CT angiographic image data; and produce a time-resolved three-dimensional image of the subject by selectively combining the three-dimensional image substantially without temporal resolution and the time-series of two-dimensional images.

18. The system of claim 17 wherein the computer system is further programmed to determine the at least one of the flow direction or the velocity of flow by determining a temporal parameter for each voxel of the time-resolved three-dimensional image.

19. The system of claim 18 wherein the temporal parameter is a mean transit time (MTT) through the vessel in the patient.

20. The system of claim 17 wherein the computer system is further programmed to superimpose a color coded display of the temporal parameter on at least one of the time-resolved three-dimensional image and a blood volume image generated from the three-dimensional image substantially without temporal resolution to combine the at least one of the flow direction or the velocity of flow with the vessel in the patient with the CT image of the patient.

21. The system of claim 16 wherein the computer system is further programmed to calculate a mean transit time (MTT) through the vessel in the patient to determine at least one of a flow direction or a velocity of flow with a vessel in the patient.

22. A system for generating quantitative computed tomography (CT) angiographic images, the system comprising:
a rotatable gantry including a radiation source and a detector coupled thereto, wherein the rotatable gantry is configured to receive a patient to rotate the radiation source and the detector around the patient to acquire a set of projection views forming CT angiographic image data of the patient using projection duration of less than 50 milliseconds;
a computer system programed to receive the CT angiographic image data from the detector and generate quantitative CT angiographic images by:
producing a composite image that indicates an attenuation value at each composite image pixel of the patient;
reconstructing the quantitative CT angiographic images of the patient by;
backprojecting each projection view in the CT angiographic image data and weighting a value backprojected into at image pixel by an attenuation value of a corresponding pixel in the composite image;
summing backprojected values for each image pixel to produce a CT image of the patient;
performing a scatter correction on at least one of the CT angiographic image data and the CT image of the patient;
determining at least one of a flow direction or a velocity of flow with a vessel in the patient;
combining the at least one of the flow direction or the velocity of flow with the vessel in the patient with the CT image of the patient to generate the quantitative CT angiographic images;
wherein, to perform the scatter correction, the computer system is further programmed to:
convolve the CT image of the patient with a blurring kernel to create a scatter image;
at each point in the CT image of the patient, estimate a scatter fraction; and
subtract the scatter image from the CT image of the patient using the scatter fraction.

23. The system of claim 22 wherein the scatter image is spatially dependent to have larger values in regions of low signal intensity in the angiographic image data.

24. The system of claim 22 wherein computer system is further programmed to estimate the scatter fraction using lead blocker data or a look-up table of scatter fraction vs. detected intensity.

25. A system for generating quantitative computed tomography (CT) angiographic images, the system comprising:
a rotatable gantry including a radiation source and a detector coupled thereto, wherein the rotatable gantry is configured to receive a patient to rotate the radiation source and the detector around the patient to acquire a set of projection views forming CT angiographic image data of the patient using a projection duration of less than 50 milliseconds;
a computer system programmed to receive the CT angiographic image data from the detector and generate quantitative CT angiographic images by:
producing a composite image that indicates an attenuation value at each composite image pixel of the patient;
reconstructing the quantitative CT angiographic images of the patient by;
backprojecting each projection view in the CT angiographic image data and weighting a value backprojected into at image pixel by an attenuation value of a corresponding pixel in the composite image;
summing backprojected values for each image pixel to produce a CT image of the patient;
performing a scatter correction on at least one of the CT angiographic image data and the CT image of the patient;
determining at least one of a flow direction or a velocity of flow with a vessel in the patient;
combining the at least one of the flow direction or the velocity of flow with the vessel in the patient with the CT image of the patient to generate the quantitative CT angiographic images;
wherein the computer system is further programmed to:
determine a centerline for the vessel in the patient using the CT image of the patient;
generate signal vs. time curves for a plurality of points along the centerline of the vessel;
convolve the signal vs. time curves with a temporal kernel to reduce effects of pulsatility;
calculate a conrise for a plurality of positions along the vessel in the patient; and
calculate the MTT through the vessel in the patient over an interval selected based on the conrise for each of the plurality of positions.

26. The system of claim 25 wherein the computer system is further programmed to generate the temporal kernel using a plurality of image frames from the CT angiographic image data.

27. The system of claim 25 wherein the computer system is further programmed to generate a MTT curve based on the MTT through the vessel across the plurality of positions and derive velocity using a slope of the MTT curve.

28. The system of claim 16 wherein the detector may include a detector array configured to acquire at least 256 slices simultaneously.

29. The system of claim 16 wherein the computer system is further programmed to derive information about a movement of the patient through the gantry when acquiring the set of projection views forming CT angiographic image data and adjust a magnification of each projection relative to the detector as the patient moves through the gantry.

30. The system of claim 16 wherein the computer system is further programmed to produce a series of intermediate composite images that progress along with the additional projection views forming CT angiographic image data.

31. A method for generating quantitative computed tomography (CT) angiographic images, the method comprising:
acquiring a set of projection views forming CT angiographic image data of a patient using a projection duration of less than 50 milliseconds;
producing a composite image from the CT angiographic image data that indicates an attenuation value at each composite image pixel of the patient;
backprojecting each projection view in the CT angiographic image data and weighting a value backprojected into at image pixel by an attenuation value of a corresponding pixel in the composite image;
summing backprojected values for each image pixel to produce a CT image of the patient;
determining at least one of a flow direction or a velocity of flow with a vessel in the patient by:
determining a centerline for the vessel in the patient using the CT image of the patient;
generating signal vs. time curves for a plurality of points along the centerline of the vessel;
convolving the signal vs. time curves with a temporal kernel to reduce effects of pulsatility;
calculating a conrise for a plurality of positions along the vessel in the patient;
calculating a meant transit time (MTT) through the vessel in the patient over an interval selected based on the conrise for each of the plurality of positions; and
displaying the at least one of the flow direction or the velocity of flow with the vessel in the patient with the CT image of the patient to provide the quantitative CT angiographic images.

32. The method of claim 31 further comprising performing a scatter correction on at least one of the CT angiographic image data and the CT image of the patient.

33. The method of claim 31 wherein the projection duration is not greater than 1 millisecond.

* * * * *

UNITED STATES PATENT AND TRADEMARK OFFICE
CERTIFICATE OF CORRECTION

PATENT NO. : 10,368,818 B2  
APPLICATION NO. : 15/723125  
DATED : August 6, 2019  
INVENTOR(S) : Charles Mistretta et al.

Page 1 of 1

It is certified that error appears in the above-identified patent and that said Letters Patent is hereby corrected as shown below:

On the Title Page

In the Title, Item (54), "ANGIOGRAPY" should be --ANGIOGRAPHY--.

In the Claims

Column 29, Claim 10, Line 21, "by ban attenuation" should be --by an attenuation--.

Column 29, Claim 10, Line 23, "image to" should be --image pixel to--.

Column 31, Claim 22, Line 30, "using projection" should be --using a projection--.

Signed and Sealed this  
Fifth Day of November, 2019

Andrei Iancu  
*Director of the United States Patent and Trademark Office*